(12) United States Patent
Hunter et al.

(10) Patent No.: US 7,547,556 B2
(45) Date of Patent: Jun. 16, 2009

(54) METHODS FOR FILING A SAMPLE ARRAY BY DROPLET DRAGGING

(75) Inventors: Ian Hunter, Lincoln, MA (US); Colin J. H. Brenan, Marblehead, MA (US); Tanya S. Kanigan, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 893 days.

(21) Appl. No.: 10/958,969

(22) Filed: Oct. 5, 2004

(65) Prior Publication Data

US 2005/0079105 A1  Apr. 14, 2005

Related U.S. Application Data

(60) Division of application No. 10/820,679, filed on Apr. 8, 2004, which is a division of application No. 09/850,123, filed on May 7, 2001, now Pat. No. 6,893,877, and a continuation-in-part of application No. 09/225,583, filed on Jan. 5, 1999, now Pat. No. 6,387,331.

(60) Provisional application No. 60/239,538, filed on Oct. 10, 2000, provisional application No. 60/071,179, filed on Jan. 12, 1998.

(51) Int. Cl.
*G01N 1/10* (2006.01)

(52) U.S. Cl. .................. 436/180; 422/100; 436/43; 436/164; 436/166; 436/171; 436/172; 436/179; 436/183

(58) Field of Classification Search ............ 356/244, 356/246; 359/599, 886; 362/318, 342, 354–356; 422/56–58, 82.05–82.09, 100, 102, 104; 436/43, 164–166, 171–172, 174, 179–180, 436/183; 506/34

See application file for complete search history.

(56) References Cited

U.S. PATENT DOCUMENTS

| | | | |
|---|---|---|---|
| 1,236,137 A | | 8/1917 | Bastow |
| 2,745,001 A | | 5/1956 | Guth |
| 2,771,398 A | | 11/1956 | Snyder |
| 3,043,669 A | * | 7/1962 | Charles ............... 422/56 |
| 3,170,980 A | | 2/1965 | Pritchard |
| 3,864,512 A | | 2/1975 | Meadow |
| 3,873,268 A | | 3/1975 | McKie, Jr. ............. 23/230 R |

(Continued)

FOREIGN PATENT DOCUMENTS

DE   100 46 224   3/2002

(Continued)

OTHER PUBLICATIONS

Hong, M.-H. et al, Applied Physics Letter 2000, 77, 2604-2606.*

(Continued)

*Primary Examiner*—Arlen Soderquist
(74) *Attorney, Agent, or Firm*—Edwards Angell Palmer & Dodge LLP; Brian R. Landry; Christine C. O'Day

(57) ABSTRACT

A method and an array filling system for loading a plurality of disparate sample containers, the sample containers comprising an integral structure. Each receptacle is characterized by a hydrophilic surface, and the receptacles are separated by a hydrophobic surface. The system has a liquid transfer device capable of holding liquid and adapted for motion to cause sequential communication of liquid held in the liquid transfer device with successive receptacles of the array by dragging the liquid across the hydrophobic surface.

20 Claims, 29 Drawing Sheets

U.S. PATENT DOCUMENTS

| | | | |
|---|---|---|---|
| 3,894,512 A | 7/1975 | Ohno | 118/637 |
| 3,997,396 A | 12/1976 | Delente | |
| 4,007,010 A * | 2/1977 | Woodbridge, III | 422/50 |
| 4,065,263 A * | 12/1977 | Woodbridge, III | 422/57 |
| 4,110,165 A | 8/1978 | Cole et al. | |
| 4,111,754 A | 9/1978 | Park | 195/127 |
| 4,273,877 A * | 6/1981 | Anagnostopoulos | 435/286.3 |
| 4,415,732 A | 11/1983 | Caruthers et al. | |
| 4,446,239 A | 5/1984 | Tsuji et al. | 436/532 |
| 4,453,805 A | 6/1984 | Ashkin et al. | |
| 4,458,066 A | 7/1984 | Caruthers et al. | |
| 4,493,815 A | 1/1985 | Fernwood et al. | 422/101 |
| 4,500,707 A | 2/1985 | Caruthers et al. | |
| 4,562,045 A | 12/1985 | Murata | 422/102 |
| 4,586,546 A * | 5/1986 | Mezei et al. | 141/2 |
| 4,613,573 A | 9/1986 | Shibayama et al. | |
| 4,659,677 A * | 4/1987 | Glover et al. | 436/174 |
| 4,663,163 A | 5/1987 | Hou et al. | |
| 4,682,890 A | 7/1987 | de Macario et al. | 356/244 |
| 4,682,891 A | 7/1987 | de Macario et al. | |
| 4,683,195 A | 7/1987 | Mullis et al. | |
| 4,683,202 A | 7/1987 | Mullis | |
| 4,701,304 A | 10/1987 | Horn et al. | |
| 4,722,515 A * | 2/1988 | Ham | 261/142 |
| 4,734,192 A | 3/1988 | Champion et al. | |
| 4,828,386 A | 5/1989 | Matkovich et al. | 356/246 |
| 4,834,946 A * | 5/1989 | Levin | 422/101 |
| 4,861,448 A | 8/1989 | Cantor et al. | |
| 4,861,722 A | 8/1989 | Sano et al. | |
| 4,869,114 A * | 9/1989 | Kido et al. | 73/864.24 |
| 4,893,886 A | 1/1990 | Ashkin et al. | |
| 4,932,806 A | 6/1990 | Eklund et al. | |
| 4,965,188 A | 10/1990 | Mullis et al. | |
| 4,973,679 A | 11/1990 | Caruthers et al. | |
| 4,990,459 A * | 2/1991 | Maeda et al. | 436/178 |
| 5,000,921 A | 3/1991 | Hanaway et al. | 422/100 |
| 5,009,846 A * | 4/1991 | Gavet et al. | 422/56 |
| 5,038,852 A | 8/1991 | Johnson et al. | |
| 5,041,266 A * | 8/1991 | Fox | 422/102 |
| 5,047,215 A | 9/1991 | Manns | 422/101 |
| 5,100,627 A | 3/1992 | Buican et al. | |
| 5,108,704 A | 4/1992 | Bowers et al. | 422/70 |
| 5,108,926 A * | 4/1992 | Klebe | 435/286.4 |
| 5,152,060 A | 10/1992 | Schubert et al. | |
| 5,153,319 A | 10/1992 | Caruthers et al. | |
| 5,175,209 A | 12/1992 | Beattie et al. | |
| 5,192,980 A | 3/1993 | Dixon et al. | |
| 5,204,268 A * | 4/1993 | Matsumoto | 436/44 |
| 5,210,021 A | 5/1993 | Goodwin, Jr. | 435/29 |
| 5,215,593 A | 6/1993 | Nojo et al. | |
| 5,219,727 A | 6/1993 | Wang et al. | |
| 5,229,163 A | 7/1993 | Fox | |
| 5,234,665 A | 8/1993 | Ohta et al. | |
| 5,234,666 A | 8/1993 | Suzuki et al. | |
| 5,242,974 A | 9/1993 | Holmes | |
| 5,262,128 A * | 11/1993 | Leighton et al. | 422/100 |
| 5,284,753 A | 2/1994 | Goodwin, Jr. | 435/30 |
| 5,290,705 A | 3/1994 | Davis | 436/164 |
| 5,310,652 A | 5/1994 | Gelfand et al. | |
| 5,322,019 A | 6/1994 | Hyland | |
| 5,322,770 A | 6/1994 | Gelfand | |
| 5,333,675 A | 8/1994 | Mullis et al. | |
| 5,373,803 A | 12/1994 | Noguchi et al. | |
| 5,374,525 A | 12/1994 | Lalouel et al. | |
| 5,382,985 A | 1/1995 | Becker et al. | |
| 5,407,800 A | 4/1995 | Gelfand et al. | |
| 5,411,876 A | 5/1995 | Bloch et al. | |
| 5,427,908 A | 6/1995 | Dower et al. | |
| 5,433,975 A | 7/1995 | Roberts et al. | |
| 5,443,791 A * | 8/1995 | Cathcart et al. | 422/65 |
| 5,445,934 A | 8/1995 | Fodor et al. | |
| 5,453,252 A | 9/1995 | Truett | 422/104 |
| 5,455,008 A | 10/1995 | Earley et al. | |
| 5,466,583 A * | 11/1995 | Thomson et al. | 435/30 |
| 5,475,610 A | 12/1995 | Atwood et al. | |
| 5,476,744 A | 12/1995 | Anno et al. | |
| 5,476,774 A | 12/1995 | Wang et al. | |
| 5,491,083 A | 2/1996 | Arentzen et al. | |
| 5,492,806 A | 2/1996 | Drmanac et al. | |
| 5,504,007 A | 4/1996 | Haynes | |
| 5,506,141 A | 4/1996 | Weinreb et al. | 435/309.1 |
| 5,508,197 A | 4/1996 | Hansen et al. | |
| 5,508,200 A | 4/1996 | Tiffany et al. | 436/44 |
| 5,510,270 A | 4/1996 | Fodor et al. | |
| 5,519,218 A | 5/1996 | Chang | 250/339.07 |
| 5,525,464 A | 6/1996 | Drmanac et al. | |
| 5,538,848 A | 7/1996 | Livak et al. | |
| 5,554,339 A | 9/1996 | Cozzette et al. | |
| 5,560,811 A | 10/1996 | Briggs et al. | 204/451 |
| 5,561,058 A | 10/1996 | Gelfand et al. | |
| 5,561,071 A | 10/1996 | Hollenberg et al. | |
| 5,576,220 A | 11/1996 | Hudson et al. | |
| 5,580,717 A | 12/1996 | Dower et al. | |
| 5,585,275 A | 12/1996 | Hudson et al. | |
| 5,593,839 A | 1/1997 | Hubbell et al. | |
| 5,599,664 A | 2/1997 | Schwartz | |
| 5,602,756 A | 2/1997 | Atwood et al. | |
| 5,605,662 A | 2/1997 | Heller et al. | |
| 5,621,094 A | 4/1997 | Roser et al. | |
| 5,632,957 A | 5/1997 | Heller et al. | |
| 5,641,391 A | 6/1997 | Hunter et al. | |
| 5,656,493 A | 8/1997 | Mullis et al. | |
| 5,667,972 A | 9/1997 | Drmanac et al. | |
| 5,710,381 A | 1/1998 | Atwood et al. | |
| 5,720,923 A | 2/1998 | Haff et al. | |
| 5,722,370 A | 3/1998 | Koike et al. | |
| 5,744,101 A | 4/1998 | Fodor et al. | |
| 5,763,263 A | 6/1998 | Dehlinger | 435/287 |
| 5,770,440 A | 6/1998 | Berndt | 435/288.4 |
| 5,770,860 A | 6/1998 | Franzen et al. | |
| 5,773,238 A | 6/1998 | Shukla | |
| 5,780,233 A | 7/1998 | Guo et al. | |
| 5,785,926 A | 7/1998 | Seubert et al. | |
| 5,786,226 A | 7/1998 | Böcker et al. | 436/164 |
| 5,795,748 A | 8/1998 | Cottingham | |
| 5,807,522 A | 9/1998 | Brown et al. | |
| 5,840,862 A | 11/1998 | Bensimon et al. | |
| 5,843,767 A | 12/1998 | Beattie | 437/287.1 |
| 5,849,598 A | 12/1998 | Wilson et al. | 436/180 |
| 5,856,100 A | 1/1999 | Hayashizaki | |
| 5,871,908 A | 2/1999 | Henco et al. | |
| 5,879,632 A | 3/1999 | Demers | |
| 5,888,723 A | 3/1999 | Sutton et al. | |
| 5,897,842 A | 4/1999 | Dunn et al. | |
| 5,906,683 A | 5/1999 | Chen et al. | |
| 5,910,287 A | 6/1999 | Cassin et al. | |
| 5,922,604 A | 7/1999 | Stapleton et al. | |
| 5,928,907 A | 7/1999 | Woudenberg et al. | |
| 5,929,208 A | 7/1999 | Heller et al. | |
| 5,942,432 A | 8/1999 | Smith et al. | |
| 5,944,652 A | 8/1999 | Miller et al. | |
| 5,955,377 A | 9/1999 | Maul et al. | |
| 5,958,345 A | 9/1999 | Turner et al. | |
| 5,962,316 A | 10/1999 | Beach et al. | |
| 5,985,214 A | 11/1999 | Stylli et al. | 422/65 |
| 5,994,056 A | 11/1999 | Higuchi | |
| 6,001,586 A | 12/1999 | Schellenberger | |
| 6,004,744 A | 12/1999 | Goelet et al. | |
| 6,015,880 A | 1/2000 | Baldeschwieler et al. | |
| 6,020,141 A | 2/2000 | Pantoliano et al. | |
| 6,024,925 A * | 2/2000 | Little et al. | 422/100 |
| 6,027,873 A | 2/2000 | Schellenberger et al. | 435/4 |
| 6,060,240 A | 5/2000 | Kamb et al. | |
| 6,071,702 A | 6/2000 | Yamamoto et al. | |

| | | | |
|---|---|---|---|
| 6,071,748 A | 6/2000 | Modlin et al. | |
| 6,083,682 A | 7/2000 | Campbell et al. | |
| 6,083,763 A | 7/2000 | Balch | |
| 6,086,825 A | 7/2000 | Sundberg et al. | |
| 6,088,100 A | 7/2000 | Brenan et al. | |
| 6,090,251 A | 7/2000 | Sundberg et al. | |
| 6,103,199 A | 8/2000 | Bjornson et al. | |
| 6,103,479 A | 8/2000 | Taylor | |
| 6,107,059 A | 8/2000 | Hart | |
| 6,121,048 A * | 9/2000 | Zaffaroni et al. | 506/14 |
| 6,136,566 A | 10/2000 | Sands et al. | |
| 6,136,592 A | 10/2000 | Leighton | |
| H001919 H | 11/2000 | Caspar et al. | |
| 6,147,198 A | 11/2000 | Schwartz | |
| 6,149,815 A | 11/2000 | Sauter | |
| 6,174,670 B1 | 1/2001 | Wittwer et al. | |
| 6,197,563 B1 | 3/2001 | Erlich et al. | |
| 6,235,473 B1 | 5/2001 | Friedman et al. | |
| 6,245,505 B1 | 6/2001 | Todd et al. | |
| 6,251,343 B1 | 6/2001 | Dubrow et al. | |
| 6,271,024 B1 | 8/2001 | Sve et al. | |
| 6,284,113 B1 | 9/2001 | Bjornson et al. | |
| 6,296,702 B1 | 10/2001 | Bryning et al. | |
| 6,306,578 B1 | 10/2001 | Schellenberger et al. | |
| 6,309,600 B1 | 10/2001 | Hunter | |
| 6,309,828 B1 | 10/2001 | Schleifer et al. | |
| 6,312,103 B1 | 11/2001 | Haluzak | |
| 6,337,435 B1 | 1/2002 | Chu et al. | |
| 6,353,774 B1 | 3/2002 | Goldenberg et al. | |
| 6,387,331 B1 | 5/2002 | Hunter | 422/102 |
| 6,391,559 B1 | 5/2002 | Brown et al. | |
| 6,399,396 B1 | 6/2002 | Bass | |
| 6,399,952 B1 | 6/2002 | Maher et al. | |
| 6,404,166 B1 | 6/2002 | Puchianu et al. | |
| 6,406,869 B1 | 6/2002 | Glickman et al. | |
| 6,410,331 B1 | 6/2002 | Schultz et al. | |
| 7,332,271 B2 | 6/2002 | O'Keefe et al. | |
| 6,429,025 B1 | 8/2002 | Parce et al. | |
| 6,436,632 B2 | 8/2002 | Schellenberger et al. | |
| 6,454,924 B2 | 9/2002 | Jedrzejewski et al. | |
| 6,485,690 B1 | 11/2002 | Pfost et al. | |
| 6,485,944 B1 | 11/2002 | Church et al. | |
| 6,495,104 B1 | 12/2002 | Unno et al. | |
| 6,503,757 B1 | 1/2003 | Chow | |
| 6,514,750 B2 | 2/2003 | Bordenkircher et al. | |
| 6,544,737 B1 | 4/2003 | Blumenfeld et al. | |
| 6,565,813 B1 | 5/2003 | Garyantes | |
| 6,572,828 B1 | 6/2003 | Potyrailo et al. | |
| 6,576,478 B1 | 6/2003 | Wagner et al. | |
| 6,579,358 B2 | 6/2003 | Delucas et al. | |
| 6,582,914 B1 | 6/2003 | Caldwell et al. | |
| 6,630,835 B2 | 10/2003 | Cheng et al. | |
| 6,638,761 B2 | 10/2003 | Shin et al. | |
| 6,642,000 B1 | 11/2003 | Strizhkov et al. | |
| 6,649,402 B2 | 11/2003 | Van der Weide et al. | |
| 6,664,044 B1 | 12/2003 | Sato et al. | |
| 6,677,151 B2 | 1/2004 | Sandell | |
| 6,682,702 B2 | 1/2004 | Barth et al. | |
| 6,689,323 B2 | 2/2004 | Fisher et al. | |
| 6,703,236 B2 | 3/2004 | Atwood | |
| 6,706,538 B1 | 3/2004 | Karg et al. | |
| 6,713,309 B1 | 3/2004 | Anderson et al. | |
| 6,716,629 B2 | 4/2004 | Hess et al. | |
| 6,730,883 B2 | 5/2004 | Brown et al. | |
| 6,737,026 B1 | 5/2004 | Bergh et al. | |
| 6,743,633 B1 | 6/2004 | Hunter | |
| 6,812,030 B2 | 11/2004 | Ozbal et al. | |
| 6,821,486 B1 | 11/2004 | Akporiaye et al. | |
| 6,841,663 B2 | 1/2005 | Lefkowitz et al. | |
| 6,844,161 B2 | 1/2005 | Siani et al. | |
| 6,848,462 B2 | 2/2005 | Covington et al. | |
| 6,878,554 B1 | 4/2005 | Schermer et al. | |
| 6,893,877 B2 | 5/2005 | Hunter et al. | |
| 7,223,363 B2 | 5/2007 | McNeely et al. | |
| 7,300,798 B2 | 11/2007 | Perbost et al. | |
| 2001/0053334 A1 | 12/2001 | Chen et al. | |
| 2001/0055765 A1 | 12/2001 | O'Keefe et al. | |
| 2002/0001544 A1 | 1/2002 | Hess et al. | |
| 2002/0001546 A1 | 1/2002 | Hunter et al. | |
| 2002/0003177 A1 | 1/2002 | O'Connor et al. | |
| 2002/0015994 A1 | 2/2002 | Schellenberger et al. | |
| 2002/0049196 A1 | 4/2002 | Carpino et al. | |
| 2002/0072096 A1 | 6/2002 | O'Keefe et al. | |
| 2002/0094533 A1 | 7/2002 | Hess et al. | |
| 2002/0110900 A1 | 8/2002 | Jovanovich et al. | |
| 2002/0119578 A1 | 8/2002 | Zaffaroni et al. | |
| 2002/0151040 A1 | 10/2002 | O'Keefe et al. | |
| 2002/0192716 A1 | 12/2002 | Schellenberger et al. | |
| 2003/0039585 A1 | 2/2003 | Freeman | |
| 2003/0080087 A1 | 5/2003 | Stelzle | |
| 2003/0108726 A1 | 6/2003 | Schembri et al. | |
| 2003/0119042 A1 | 6/2003 | Franco De Sarabia Rosado et al. | |
| 2003/0124716 A1 | 7/2003 | Hess et al. | |
| 2003/0170610 A1 | 9/2003 | Cima et al. | |
| 2003/0180807 A1 | 9/2003 | Hess et al. | |
| 2003/0186350 A1 | 10/2003 | Newell | |
| 2003/0207099 A1 | 11/2003 | Gillmor et al. | |
| 2003/0219716 A1 | 11/2003 | Avdeef et al. | |
| 2004/0023223 A1 | 2/2004 | Thompson et al. | |
| 2004/0037748 A1 | 2/2004 | Hasan et al. | |
| 2004/0132040 A1 | 7/2004 | Hamill | |
| 2004/0171166 A1 | 9/2004 | Hunter | |
| 2004/0191924 A1 | 9/2004 | Hunter et al. | |
| 2004/0208792 A1 | 10/2004 | Linton et al. | |
| 2004/0209303 A1 | 10/2004 | Martin | |
| 2004/0235005 A1 | 11/2004 | Friedlander et al. | |
| 2004/0241636 A1 | 12/2004 | Michnick et al. | |
| 2005/0059074 A1 | 3/2005 | Schellenberger et al. | |
| 2005/0079105 A1 | 4/2005 | Hunter et al. | |
| 2005/0130213 A1 | 6/2005 | Morrison | |
| 2005/0148066 A1 | 7/2005 | O'Keefe et al. | |
| 2006/0057209 A1 | 3/2006 | Chapman et al. | |
| 2006/0105433 A1 | 5/2006 | Bickmore et al. | |
| 2006/0183171 A1 | 8/2006 | Schellenberger et al. | |
| 2006/0194108 A1 | 8/2006 | Drews et al. | |
| 2008/0108112 A1 | 5/2008 | O'Keefe et al. | |

FOREIGN PATENT DOCUMENTS

| | | |
|---|---|---|
| EP | 0 236 069 | 9/1987 |
| EP | 0 402 888 | 12/1990 |
| EP | 0 506 993 | 4/1991 |
| EP | 0 882 593 A1 | 12/1998 |
| EP | 1 155 742 | 11/2001 |
| JP | 63107057 | 5/1988 |
| WO | WO 95/01559 | 7/1994 |
| WO | WO 95/11755 | 5/1995 |
| WO | WO-97/00941 | 1/1997 |
| WO | WO-97/00943 | 1/1997 |
| WO | WO 97/15394 | 5/1997 |
| WO | WO 97/36167 | 10/1997 |
| WO | WO-97/37036 | 10/1997 |
| WO | WO 98/45406 | 10/1998 |
| WO | WO 98/47003 | 10/1998 |
| WO | WO 99/11373 | 3/1999 |
| WO | WO 99/19510 | 4/1999 |
| WO | WO 99/34920 | 7/1999 |
| WO | WO 99/39829 | 8/1999 |
| WO | WO 99/47922 | 9/1999 |
| WO | WO 99/52560 | 10/1999 |
| WO | WO-99/55461 | 11/1999 |
| WO | WO-99/61152 A1 | 12/1999 |
| WO | WO-00/01798 | 1/2000 |
| WO | WO-00/51735 | 9/2000 |
| WO | WO 00/56456 | 9/2000 |
| WO | WO-01/38583 | 5/2001 |

| | | |
|---|---|---|
| WO | WO-01/61054 | 8/2001 |
| WO | WO-01/87335 | 11/2001 |
| WO | WO-02/26394 | 4/2002 |
| WO | WO 02/30561 | 4/2002 |
| WO | WO-02/40158 | 5/2002 |
| WO | WO-02/055199 | 7/2002 |
| WO | WO-02/078834 | 10/2002 |
| WO | WO 02/087764 | 11/2002 |
| WO | WO-02/089982 | 11/2002 |
| WO | WO 03/002226 | 1/2003 |
| WO | WO-03/035239 | 5/2003 |
| WO | WO-03/042697 | 5/2003 |
| WO | WO-2004/018104 | 3/2004 |
| WO | WO-2004/074818 A2 | 9/2004 |

OTHER PUBLICATIONS

Cadus, Cadus Pharmaceutical Corp, 1997 Annual Report, 1-29, May 8, 1998.

Wittwer et al., "*The Light Cycler: A Microvolume Multisample Fluorimeter with Rapid Temperature Control*", pp. 176-181, BioTechniques, Jan. 1997.

Erfle et al., "*Simultaneous loading of 200 sample lanes for DNA sequencing on vertical and horizontal, standard and ultrathin gels*", vol. 25, No. 11, pp. 2229-2230, Oxford University Press, 1997.

MacBeath et al., "*Printing Proteins as Microarrays for High-Throughout Function Determination*", pp. 1760-1762, vol. 289, Science, Sep. 2000.

Singh-Gasson et al., "*Maskless fabrication of light-directed oligonucleotide microarrays using a digital micromirror array*" vol. 17, pp. 974-978, Nature Biotechnology, Oct. 1999.

Vogelstein et al., "*Digital PCR*" vol. 96, pp. 9236-9241, Pro. Natl. Acad. Sci USA, Aug. 1999.

Smith et al., "*Dynamical Scaling of DNA Diffusion Coefficients*", vol. 29, pp. 1372-1373, Macromolecules, 1996.

Thorstenson et al., "*Global Analysis of ATM Polymorphism Reveals Significant Functional Constraint*", vol. 69, pp. 396-412, Am. J. Hum. Genet., 2001.

Wittwer et al., "*Continuous Fluorescence Monitoring of Rapid Cycle DNA Amplification*", vol. 22, pp. 130-138, BioTechniques, Jan. 1997.

CRC Handbook of Chemistry and Physics, Ed. Robert C. Weast, Ph.D. 65th Edition. 1984-1985. PPF-20-F-35.

Adlercreutz et al., "Oxygen Supply to Immobilized Cells," *European Journal of Applied Microbiology Biotechnology*, vol. 16 pp. 165-170 (1982).

Kanigan et al., "Living Chips for Drug Discovery", Mar. 2000, Proceedings of SPIE, vol. 3926, pp. 172-180.

Colin J. Brenan et al., "A massively parallel microfluidics platform for storage and ultra high throughput screening", 4626 Proc. SPIE 560-69 (2002).

Sosnowski, Luke, "Manufacturing Methods for High Density Micro-Channel Arrays" (Jun. 2000) (Master's Thesis) (Massachusetts Institute of Technology Dep't of Mechanical Engineering).

Prescott et al., Microbiology 31, 114-16 (1990).

J.H. Brown, Charts for Counting Bacterial Colonies, 37 Am. J. Pub. Health Nations Health 206-07 (1947).

Polokoff et al, Isolation of Somatic Cell Mutants Defective in the Biosynthesis fo Phoshatidyletanolamine, 256 J. Biological Chem. 7687-90 (1981).

Coleman et al., Phospholipid Synthesis in Isolated Fat Cells, 252 J. Biological Chem. 3050-56 (1977).

Colin S. Cooper, Applications of microarray technology in breast cancer research, 3(3) Breast Cancer Res. 158-75 (2001).

Elizabeth Zubritsky, Spotting a microarray system, 4(5) Modern Drug Discovery 59 (May 2001).

de Macario et al., "The slide immunoenzymic assay: a simple laboratory tool with multiple applications", Chemical Abstr. 67622t (1985).

de Macario et al., "Slide Immunoenzymatic Assay (SIA) in Hybridoma Technology", 121 Methods in Ezymology 509-25 (1986).

de Macario et al., "Adaptation of the Slide Immuneozymatic Assay for Quantification of DNA Hybridization: SIA-DNA", 8 Biotechniques 210-17 (1990).

L.J. Kricka & P. Wilding, Microchip PCR, 377 Anal. Bioanal. Chem. 820-25 (2003).

A.F.R. Huhmer & J.P. Landers, Noncontact Infrared-Mediated Thermocycling for Effective Polymerase Chain Reaction Amplification of DNA in Nanoliter Volumes, 72 Anal. Chem. 5507-12 (2000).

Mann A. Shoffner et al. Chip PCR. I. Surface passivation of microfabricated silicon-glss chips for PCR, 24(2) Nucleic Acids Research 375-79 (1996).

Da-Sheeng Lee et al., A novel real-time PCR machine with a miniature spectrometer for fluorescence sensing in a micro liter volue glass capillary, 100 Sensors and Actuators B 401-10 (2004).

Tian-Lu Cheng et al., "Membrane-Tethered Proteins for Basic Research, Imaging and Therapy", Medical Research Reviews (May 14, 2008).

* cited by examiner

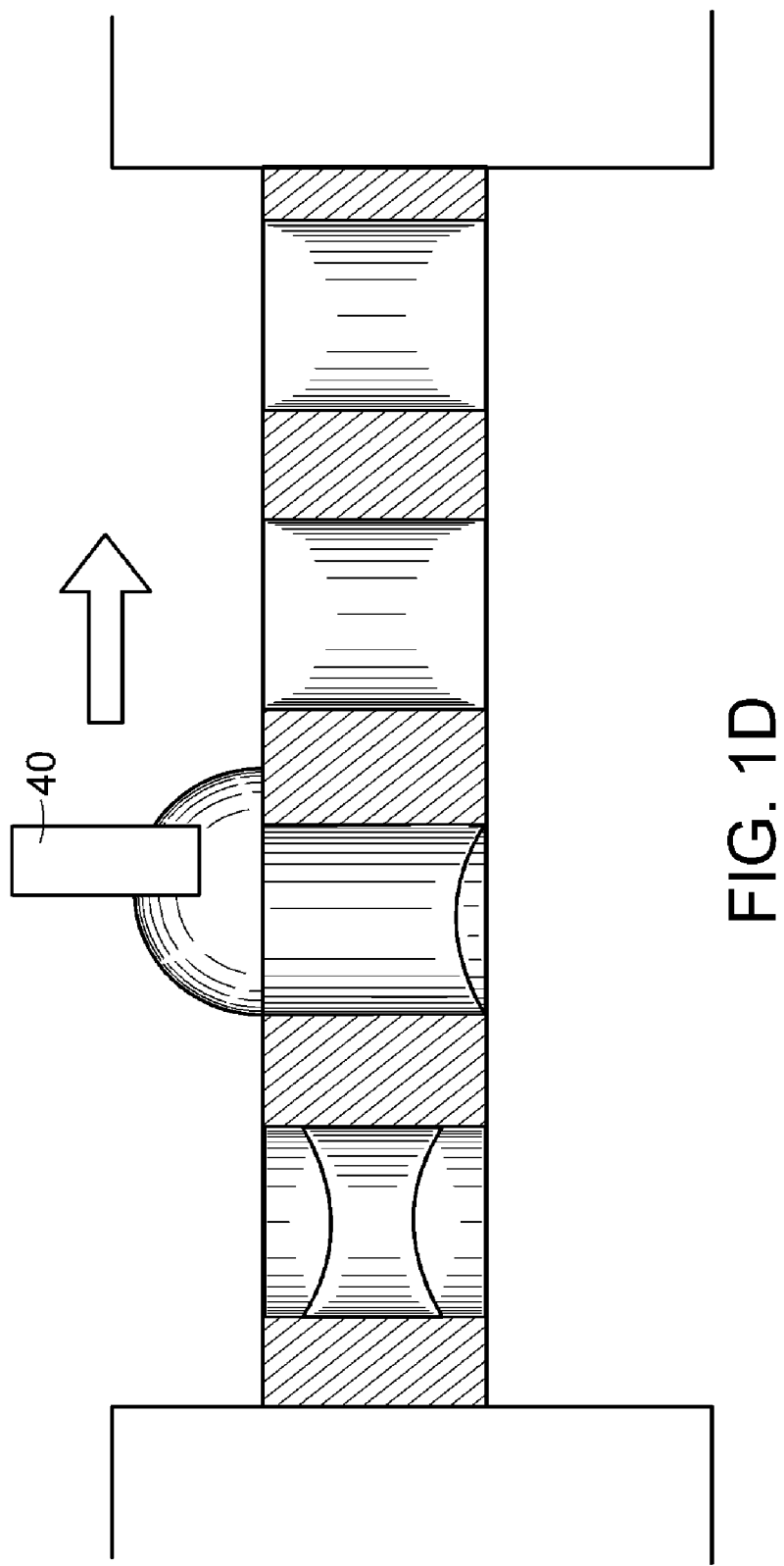

CLOSE PACKING

RECTANGULAR PACKING

US 7,547,556 B2

METHODS FOR FILING A SAMPLE ARRAY BY DROPLET DRAGGING

The present application is a divisional of copending U.S. patent application Ser. No. 10/820,679, filed Apr. 8, 2004, itself a divisional of U.S. Ser. No. 09/850,123, filed May 7, 2001, now issued as U.S. Pat. No. 6,893,877, claiming priority from U.S. Provisional Application No. 60/239,538, filed Oct. 10, 2000, and also a continuation-in-part of U.S. Ser. No. 09/225,583, filed Jan. 5,1999, now issued as U.S. Pat. No. 6,387,331 which in turn claims priority from U.S. Provisional Application No. 60/071,179, filed Jan. 12, 1998, from all of which applications the present application claims priority. Each of the above-referenced applications are herein incorporated by reference.

FIELD OF THE INVENTION

The present invention pertains to methods for manufacturing and using apparatus for manipulating, transporting, and analyzing a large number of microscopic samples of a liquid or of materials including cells currently or formerly in liquid suspension.

BACKGROUND OF THE INVENTION

Chemistry on the micro-scale, involving the reaction and subsequent analysis of quantities of reagents or analytes of order microliters or smaller, is an increasingly important aspect of the development of new substances in the pharmaceutical and other industries. Such reaction and analysis may accommodate vast libraries containing as many as a million compounds to be reacted and analyzed under various conditions. Significant problems associated with current technologies as applied to chemical analysis of vast numbers (potentially on the order of hundreds of thousands or millions per day) of compounds include the problem of handling vast numbers of compounds and reactions in parallel.

Existing technology relies on 96-, 384-, or 1536-well plates containing quantities between approximately 1 microliter and 1 milliliter of liquid compound per well, and, generally, involves chemical reactions and analysis in wells disposed with single openings on flat surfaces such as polystyrene. It is not practical to apply existing technology in the art to form million-well microtiter plates. There is a need, therefore, for new approaches that permit the analysis of a million samples in a laboratory format.

SUMMARY OF THE INVENTION

In accordance with preferred embodiments of the present invention, a method and an array filling system are provided for loading a plurality of disparate sample containers, the sample containers comprising an integral structure. In the array filling system for transferring liquid to an array of receptacles, each receptacle is characterized by a hydrophilic surface, and the receptacles are separated by a hydrophobic surface. The system has a liquid transfer device capable of holding liquid and adapted for motion to cause sequential communication of liquid held in the liquid transfer device with successive receptacles of the array by dragging the liquid across the hydrophobic surface.

In accordance with other embodiments of the invention, the array filling system has an array of liquid transfer devices capable of holding liquid, the plurality of liquid transfer devices adapted for motion to cause sequential communication of liquid held in the liquid transfer devices with successive receptacles of the array by dragging the liquid across the hydrophobic surface.

In accordance with yet other embodiments of the invention, a method is provided for transferring a liquid into an array of receptacles having hydrophilic surfaces and separated by a hydrophobic surface. The method has steps of:

a. positioning a liquid transfer device in proximity to the surface; and b. moving the fluid transfer device across the hydrophobic surface and over the receptacles to be filled so as to cause sequential communication of liquid in the liquid transfer device with the hydrophilic surface of each receptacle.

In further embodiments of the invention, the method may have a further step of withdrawing residual fluid from the surface of the platen. The step of causing communication of liquid in the liquid transfer device with the hydrophilic surfaces of the plurality of hydrophilic receptacles may include forming a droplet of the liquid on the end of a capillary, or on the end of a pipette or needle, and may, further, include transferring liquid into through-holes of an array of through-holes.

BRIEF DESCRIPTION OF THE DRAWINGS

The invention will be more readily understood by reference to the following description, taken with the accompanying drawings, in which:

FIG. 1D shows a cross-sectional view of the loading of a high-density array of through holes with a liquid transfer device in accordance with one embodiment of the present invention.

DETAILED DESCRIPTION OF SPECIFIC EMBODIMENTS

The Through-Hole Array

In accordance with the present invention, methods are provided for producing different chemical reactions within an array of through-holes. The invention is advantageously employed, for example, in screening operations, where different reaction conditions are advantageously provided among the various through-holes of the array. As an example of the many modalities of use of the invention, different chemical species may be loaded into different through-holes of the array, and concentrations of the various species might also be differentiated among the various through-holes. The invention may thus provide a method for screening compound libraries, for example, to predict the ability of each compound to be absorbed by a patient.

Figure 1A:
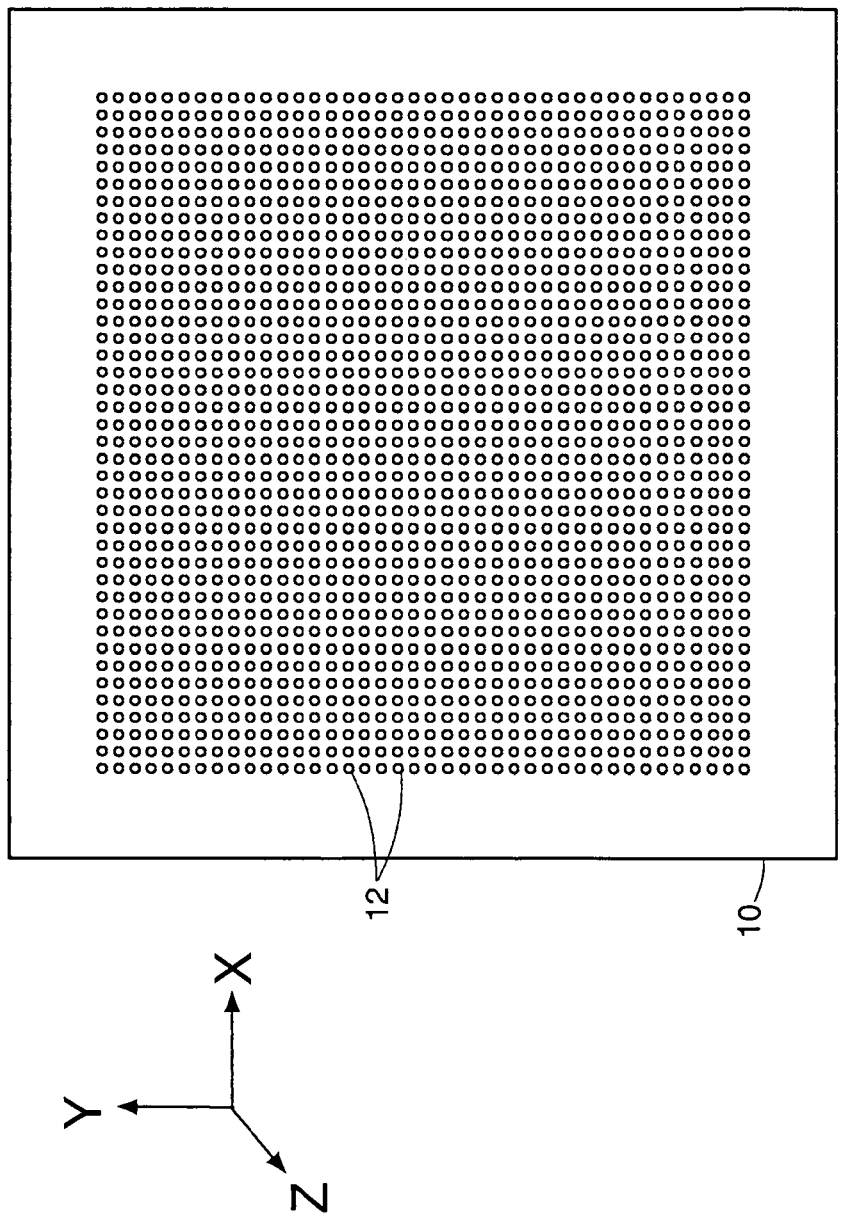
FIGS. 1a and 1b show a top and exploded cross-sectional views, respectively, of a high-density array of through-holes in accordance with one embodiment of the present invention.
Figure 1B:
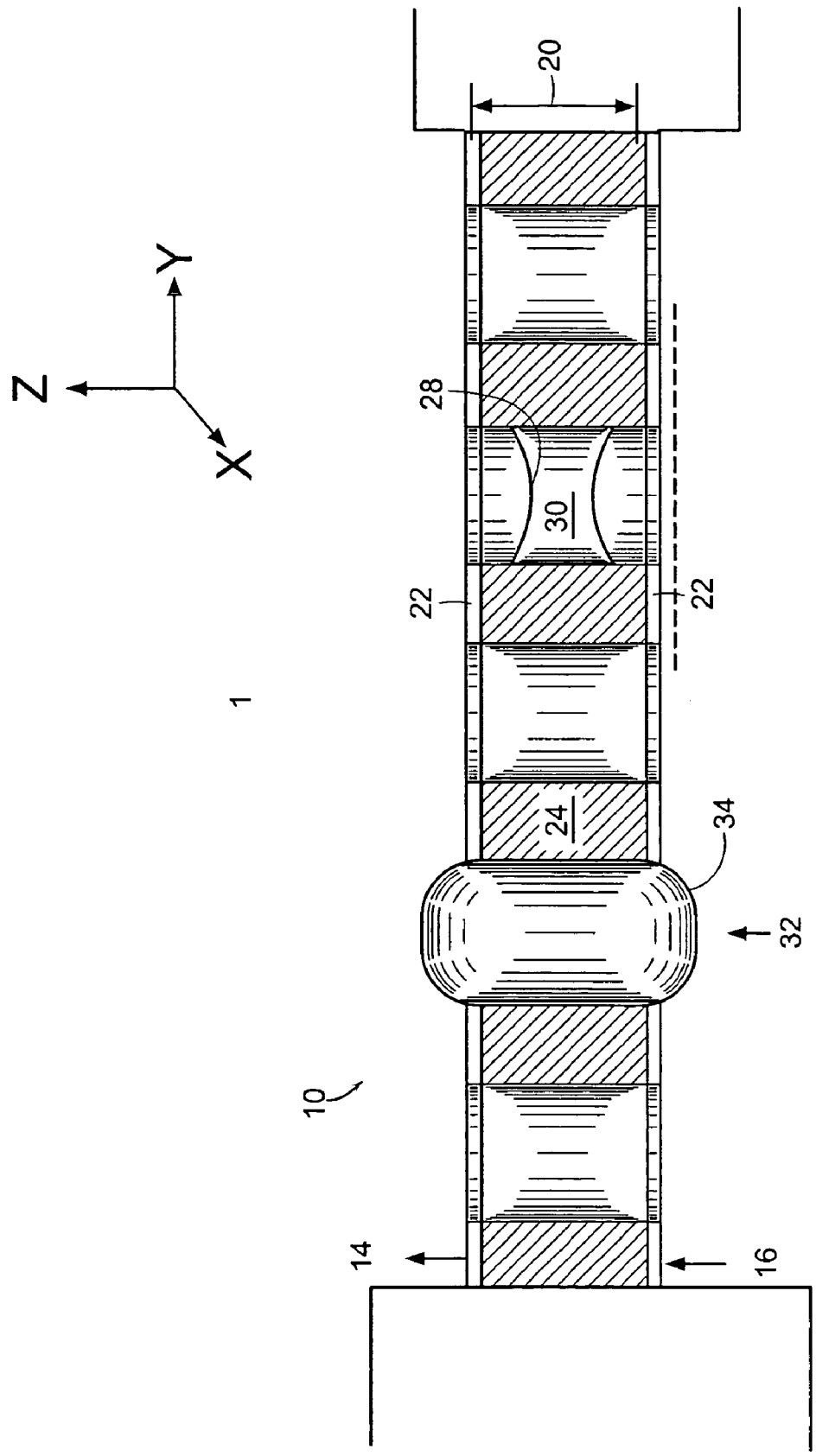

In accordance with preferred embodiments of the invention, a high-density array of through-holes is provided, as now discussed with reference to FIGS. 1*a* and 1*b*. FIG. 1*a* shows a top view of a platen 10, otherwise referred to herein as a "substrate," "sample wafer," or "through-hole plate." Platen 10 is the carrier of a large number of through-holes 12 which traverse platen 10 from a top surface 14 to an opposing surface 16 of the platen, as shown in the cross-sectional side view of FIG. 1*b*. While the term "platen" may refer to a structure having substantially parallel plane surfaces and transverse dimensions substantially exceeding the thickness of the structure, alternative geometries are within the scope of the present invention, and use of the term "platen" is not restrictive. A prism-shaped geometry is described below, for example.

Through-holes 12 constitute assay wells (or "microwells") in accordance with an embodiment of the invention. Through-holes 12 may be shaped as circular right cylinders, or, alternatively, may have rectangular cross-sections. Otherwise-shaped through-holes are also within the scope of the present invention.

While through-hole plate 10 is preferably made of conductive silicon, other types of rigid materials, such as metal, glass, or plastic may be used provided that the material is chemically inert with respect to the sample substances, or can be rendered so by appropriate surface treatments.

Each through-hole 12 is typically of a substantially square cross-section, although geometries, such as circular or rectangular cross-sections may be used. Through-holes 12 are also referred to herein as "channels."

Figure 2B:
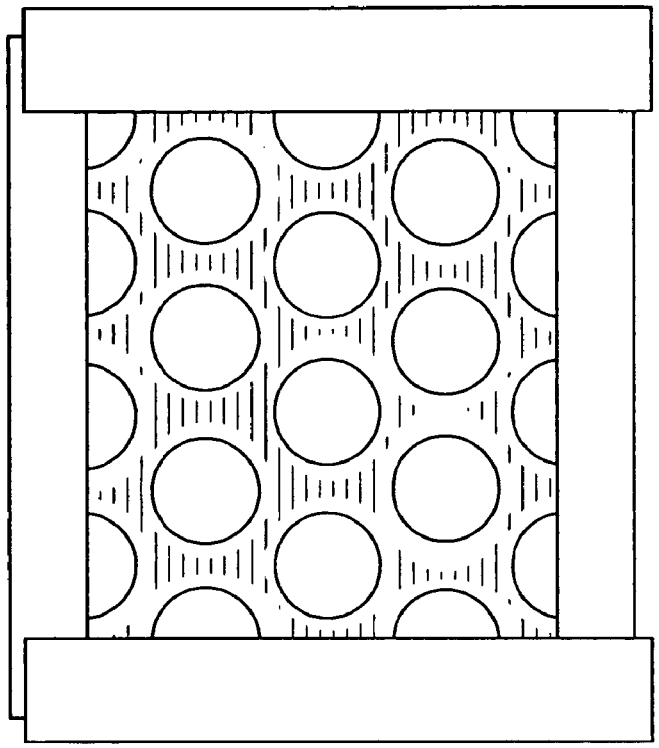
FIG. 2b is top view of a portion of the platen of FIG. 1a in which the through-holes are configured in a hexagonal close-packed array.
Figure 2A:
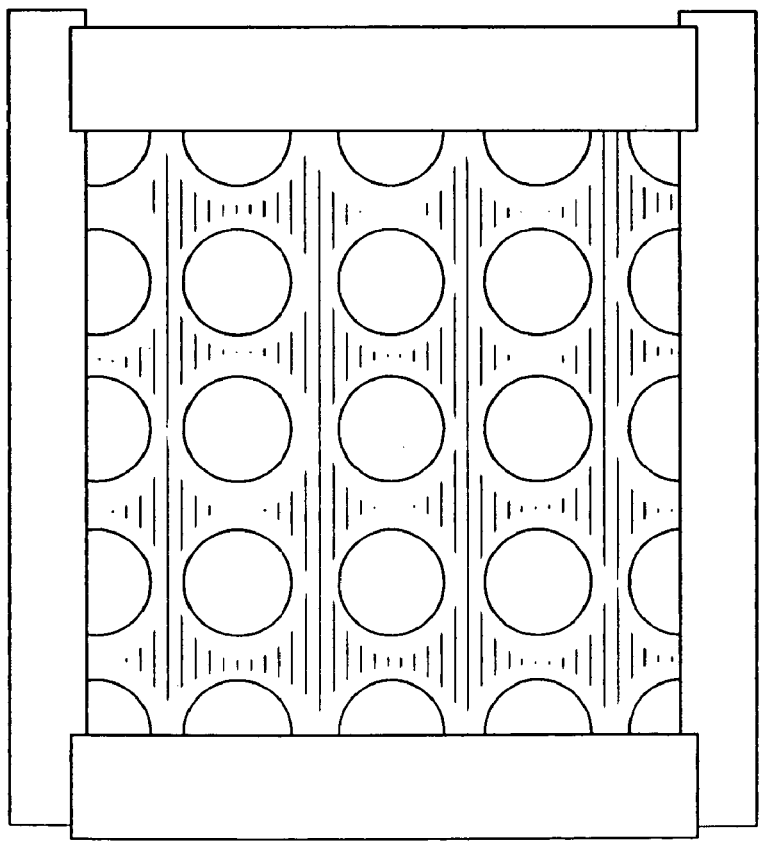
FIG. 2a is top view of a portion of the platen of FIG. 1a in which the through-holes are configured on rectangular centers.
Figure 3:
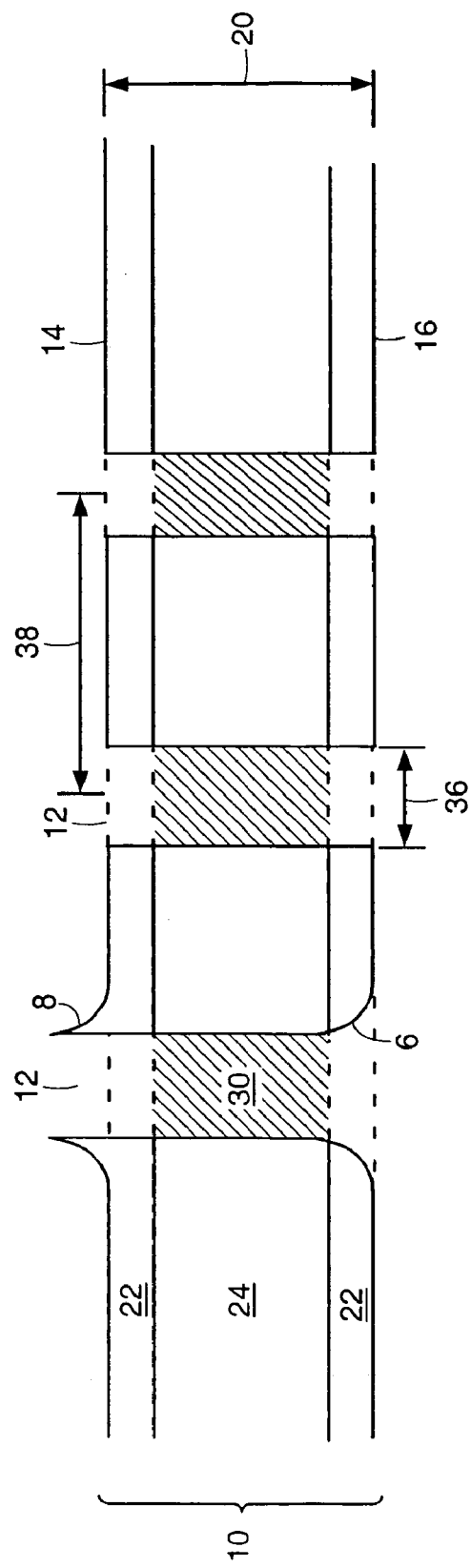
FIG. 3 is a further side view in cross-section of a portion of a laminated platen containing multiple through-holes for analysis of liquid samples in accordance with a preferred embodiment of the present invention.
Figure 4:
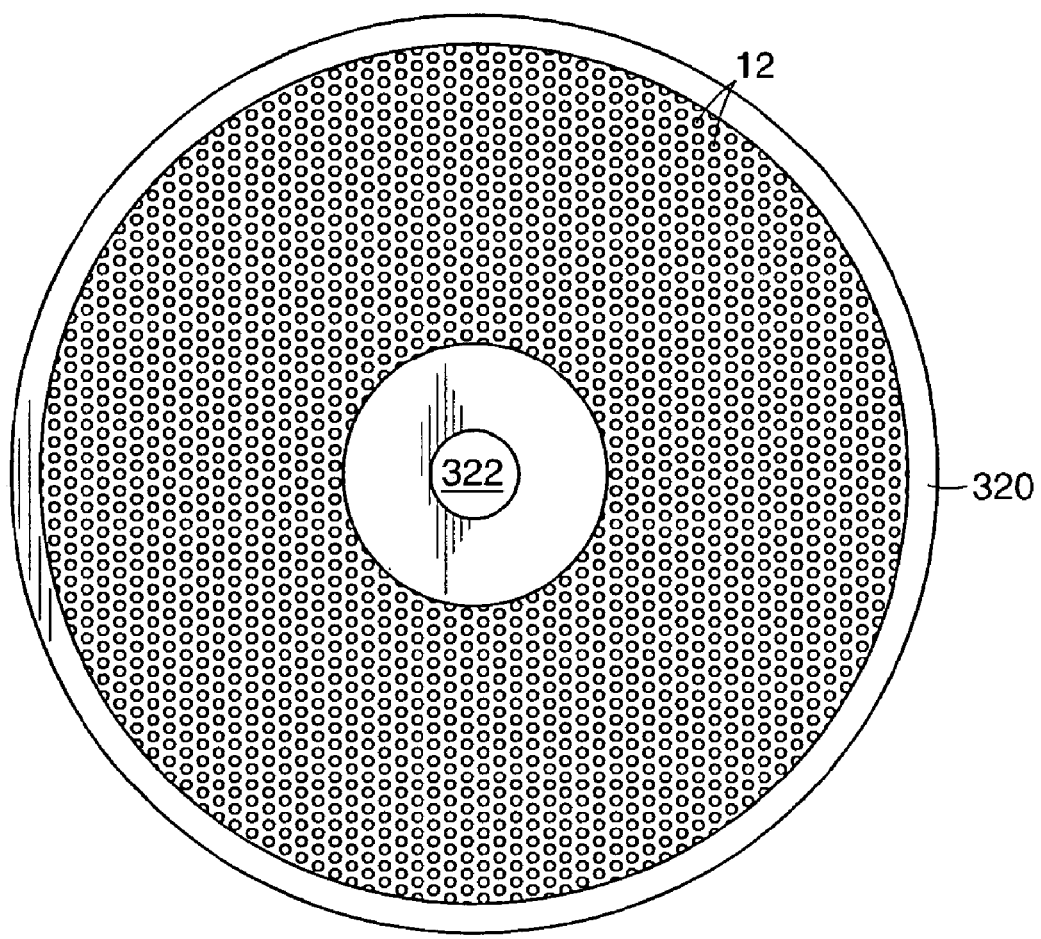
FIG. 4 is a top view of round sample wafer populated with through-holes in accordance with an embodiment of the present invention.

Through-holes 12 may be centered on a rectangular grid, as shown in FIG. 2*a*, or in a close-packed hexagonal lattice, as shown in FIG. 2*b*. Referring to FIG. 3, a typical thickness 20 of platen 10 is on the order of 0.5-2 mm, while through-holes 12 have typical characteristic dimensions (such as diameters) 36 of on the order of 100-400 μm. Thus the volume of each through-hole 12 between surface 14 and surface 16 is on the order of ~$10^{-7}$ cm$^3$ or greater. Through-holes 12 are spaced on centers typically on the order of twice the diameter of the holes, although all spacing configurations are within the scope of the invention and of the appended claims. In particular, a hole-to-hole spacing 38 of 500 μm is typically employed, which corresponds to an array density of 400 holes per square centimeter of plate. In accordance with manufacturing methods described below, microwells are produced for the assay of a chemical or biochemical reaction where the volume of each microwell may be less than 100 nanoliters ($10^{-7}$ cm$^3$). The packing density of wells may thereby be increased by several orders of magnitude over prior art technology.

Grouping of through-holes into smaller sub-arrays may also be used, and, more particularly, a reproducible pattern may be applied to a plurality of the sub-arrays. Each through-hole 12 may be identified by its own address within the array.

Referring, again, to FIG. 1*b*, platen 10 may also advantageously be formed of a laminate of materials, with a central layer 24 and outer "sandwiching" layers 22. In order to enhance capillary loading of sample 30 into the microwell and to prevent capillary outmigration of the sample liquid, exterior sections 22 of the microwell, adjacent to surfaces 14 and 16 of platen 10, have a hydrophobic wall surface in accordance with a preferred embodiment of the invention, while the interior section 24 of the through-hole wall has a hydrophilic surface thereby preferentially attracting an aqueous liquid sample. In a similar manner, an array having hydrophilic faces and hydrophobic through-holes may be uniformly filled with a low surface tension liquid such as an alkane. The hydrophobic layers on either end of the well are on the order of 1 μm thick or less. On loading the sample liquid into the microwells, each well is typically overfilled by about 10% above the volume surrounded by the four walls of the microwell. Under these circumstances, liquid sample 30 may form convex meniscus surfaces 34 on both the upper and lower surfaces of the sample.

An underfilled microwell 26 will typically be characterized by a liquid sample exhibiting a concave meniscus 28 on both the upper and lower surfaces of liquid sample 30.

The apertures of through-holes 12 need not be square, and, in accordance with an alternate embodiment of the present invention, flanges 8 may extend above planar surface 14 surrounding some or all of through-holes 12 while indentations 6 may be fabricated rounding the edges of through-holes 12 at opposing surface 16. Flanges 8 and indentations 6 may advantageously provide for registration of successive platens 10, in the case where platens are stacked, and in processes of mixing or dilution, as discussed in detail below.

Through-holes 12 may be loaded with a first sample 18 in liquid form. Sample 18 is allowed to react with a second sample where the second sample may include a variety of test samples and by subsequent or concurrent analysis of the reaction products, using, for example, optical markers, a large number of reactions may be processed and analyzed in parallel.

As applied to biological assays, by way of example, first sample 18 may be a solution containing pharmacologically relevant proteins or other molecules. Such a solution may include, for example, cells in aqueous suspension, eukaryotic (animal, yeast) or prokaryotic (bacteria) cells, hybrid cells, and biological molecules including, for example, antibodies and enzymes, although application to other biological or non-biological assays is within the scope of the invention as claimed herein. All such reagents may also be referred to herein and in the appended claims as "targets." Typical yeast cell concentrations of $10^7$ cells per milliliter of solution yield on the order of 1000 cells per 100 nanoliter well. Typically, an entire chip or the subset of through-hole wells constituting a contiguous region of platen 10 may be populated with a single strain of cells.

A typical procedure assay procedure, such as may be employed in pharmaceutical research, entails the subsequent addressed introduction of a test sample including one or more analytes into the through-hole wells, with selected materials introduced into subsets of through-holes that may include one or more through-holes. The test sample addressably introduced into the subsets of through-holes may contain drug candidates or known drugs. The test sample may be comprised of multiple components, introduced at the same time or sequentially. Components of the test sample may include analytes, antagonists, reagents, solvents, or any other materials and may be introduced in liquid form or otherwise. In accordance with a preferred embodiment of the invention, test samples are introduced into the through-hole wells in liquid form in order to facilitate rapid reaction via diffusion with first sample 18 already resident in liquid form in the through-holes.

The set of substances from which the second sample addressed to a particular through-hole site is drawn is referred to in this description and in the appended claims as a "library" of substances. In typical applications, the library is of a substantial size and thus advantageously utilizes the capability of the present invention to facilitate parallel reaction and analysis of large numbers of substances. In pharmaceutical applications in particular, libraries may be composed of between $10^3$ and $10^9$ substances and combinations of substances.

Figure 1C:
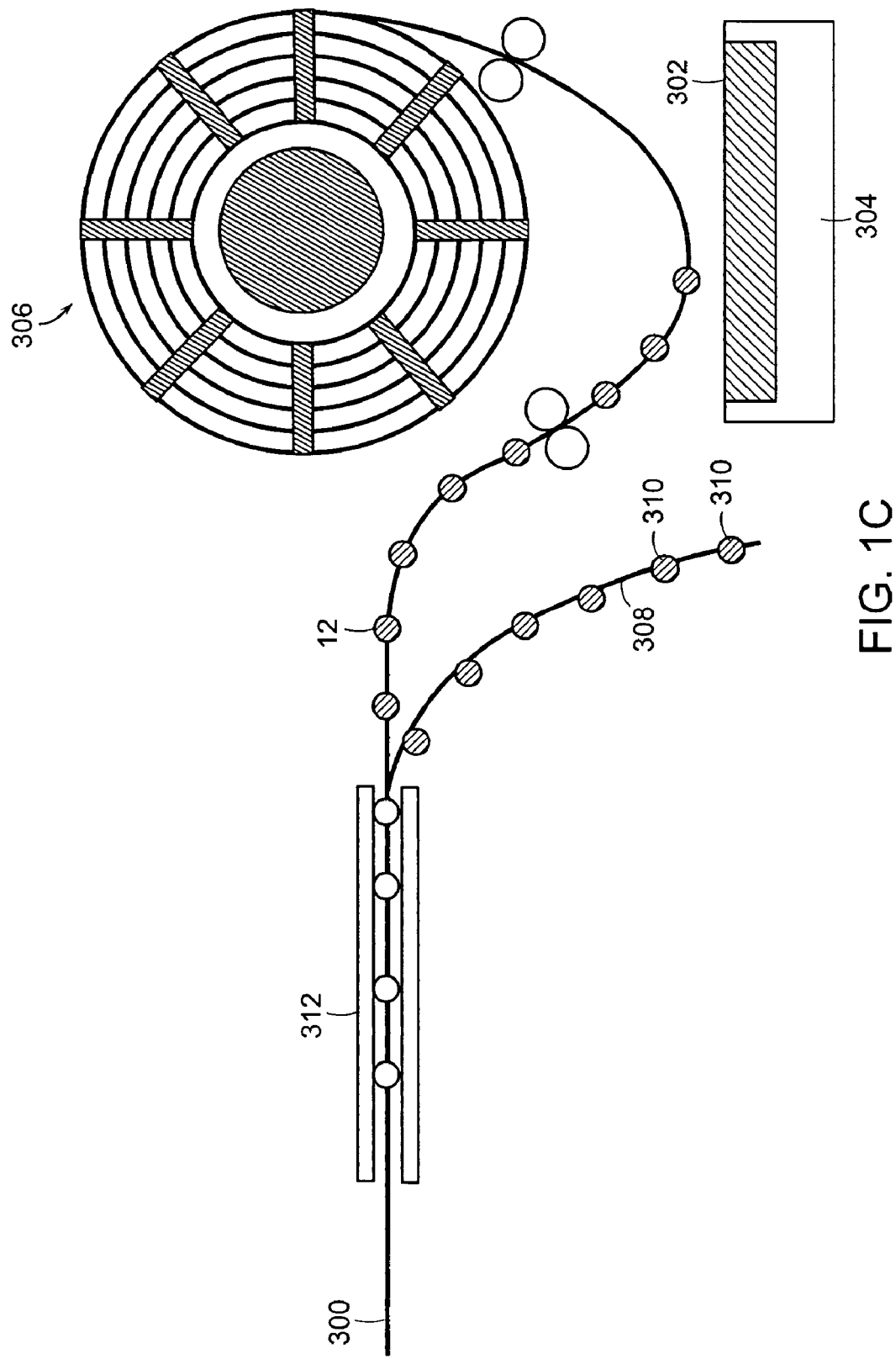
FIG. 1c shows a schematic side view of a continuous sheet array of through-holes in accordance with another embodiment of the present invention.

Referring now to FIG. 1c, the throughput of a screening system incorporating arrays of through-hole sample containers may be further increased by using a continuous sheet 300 of through-holes 12. The interiors of the through-holes may be hydrophilic, as described above in reference to FIG. 1b, and the surface of sheet 300 may be hydrophobic, as also described. Through-holes 12 may be filled in a continuous manner by passing sheet 300 through an aqueous medium 302 contained in fluid trough 304. After through-holes 12 have been filled, sheet 300 may be wound onto a spool 306 or cassette for storage followed by assay, or, alternatively, may be assayed directly. Assays may be by optical readout such as fluorescence absorbance or chemi-luminescence measurements, all of which may be performed by passing the sheet across an optical detector such as a CCD array.

Sample array sheets 300 are preferably produced with registered holes, either by precision production processes or in matched sets. The sheet composition may be a polymer, elastomer, or metal, including an amorphous metal. Multiple sheets may be mated in the same way that platens of through-holes may be stacked, as described below, for example, with reference to FIGS. 16-19, in order to initiate reactions, or for other purposes. FIG. 1c shows a second sheet 308 of through-holes 310 being brought into contact with sheet 300 in mixing area 312 for mixing of the liquid contents of the respective through-holes. Examples of applications involving this embodiment include, screening genetic libraries or screening combinatorial chemical libraries contained on polymer beads. These embodiments of the invention may advantageously include extremely high throughput, reduction or elimination of high-cost automation components, and the small size of a screening system with sample handling and detection modules. The holes in the sheet may be, if desired, produced online with an array of punches or UV lasers.

As an example of an application in which a genetic library is screened for improved enzymes using a one step assay, an *E. coli* genetic library is prepared containing mutations in the beta galactosidase enzyme. The *E. coli* cells are grown to a density in phosphate-limited media such that there is an average of 1 cell for every 200 nl of liquid. The media also contains, MUG, a fluorogenic substrate for beta-galactosidase. A through-hole sheet is prepared with a hydrophobic exterior and hydrophilic through-holes at a density of $10^7$ per square meter. Registration holes are includes in the tape to aid in precise dispensing. Each through-hole holds 70 nl of fluid. A spool of the through-hole sheet is unwound and guided through a trough containing the cell solution, so that each through hole is filled. The sheet is then wound onto spacers and into a receiving spool. The spacers prevent smearing of the liquid and provide for gas transfer in and out of the spool. The spool is incubated in a humidified enviroment at 37° C. for 24 hours. The spool is then unwound as it is passed between a uniform photo-illumination source with a wavelength of 350 nm and a CCD imaging system with a 450 nm filter. The position in the sheet of colonies with exceptionally high enzyme activity is recorded and those colonies are retrieved using a robotic microfluid handling system for further analysis. This assay can also be performed by co-registering and mating a second, identical, sheet containing the fluorogenic substrate with the first sheet containing the bacteria. An absorbance measurement may also be performed to normalize the signal output for the number of bacteria.

In accordance with another alternate embodiment of the present invention, described with reference to FIG. 3, through-holes 12 may be disposed in an array within a circular sample wafer 320 having a central hole 322 for purposes of centering with respect to handling equipment.

Referring now to FIG. 5, platen 10 and through-holes 12 may assume other geometries than have heretofore been described, in accordance with alternate embodiments of the invention. The volumes of the through-holes may be varied as a known function of spatial location in the array. The volume of a through-hole, $V=k s^2 l$, is a function of lateral hole dimension, s, length, l and constant k that depends on the specific cross-sectional hole geometry. The cross section may be varied, as depicted in FIG. 5a, as a known function of spatial location within the array by changing the hole's lateral dimensions as a function of position within the array. The hole volume scales as $s^2$; thus increasing the hole dimensions by a factor of 3.3 increases the volume by a factor of 10. One example is in a plane parallel plate, the hole dimensions are increased as a linear function in one or both lateral directions.

Figure 5A:
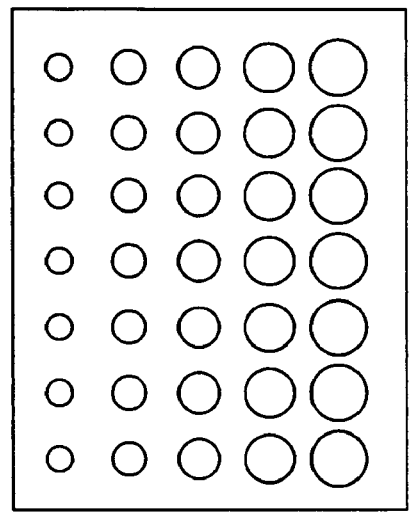
FIGS. 5a-5d show examples of arrays with through-hole volumes that are a function of array position.
Figure 5C:
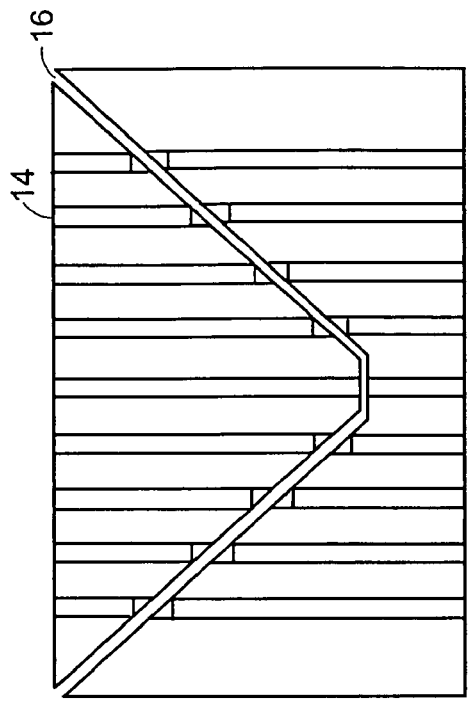
Figure 5B:
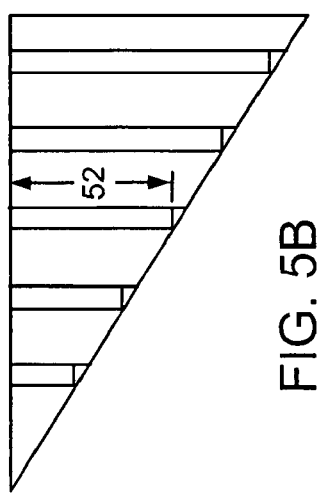
Figure 5D:
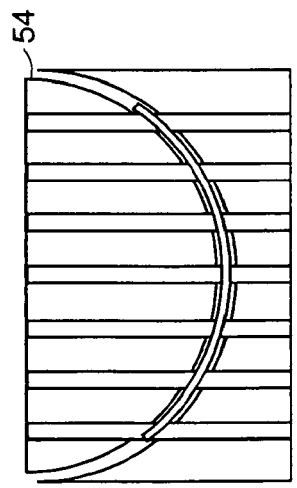
Figure 5E:
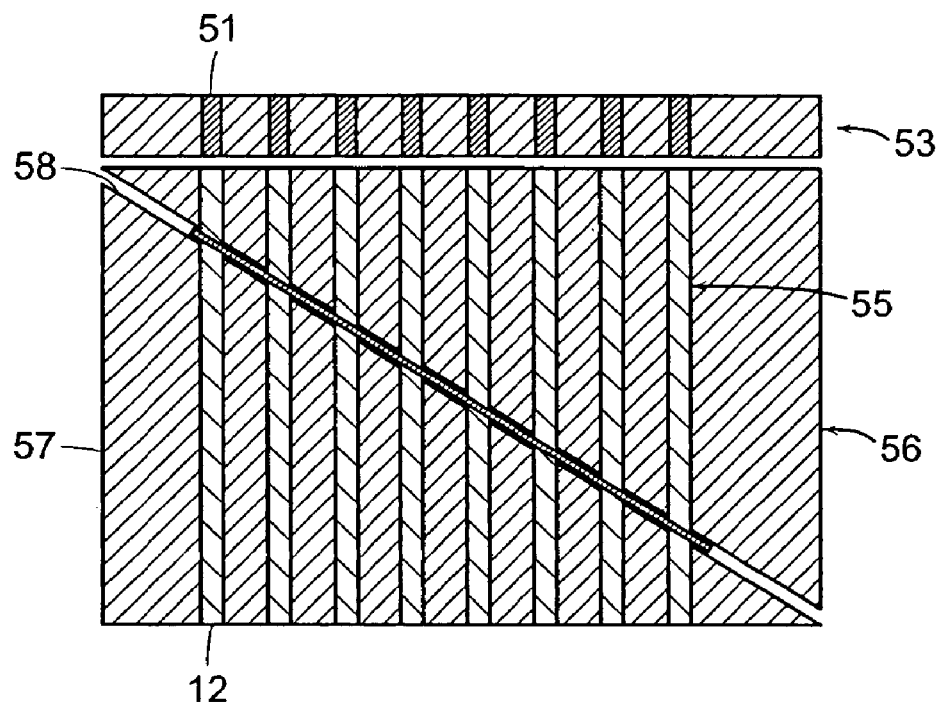
FIGS. 5e and 5f show cross sections of through-hole prisms as employed for massively parallel liquid chromatography or electrophoresis, in accordance with embodiments of the present invention.

Another method to produce different through-hole volumes as a function of array position is to change the distance between top and bottom surfaces of the plate defining the hole length 52, as shown in FIG. 5b. One particular example is to incline the plate top 14 and bottom 16 surfaces at an angle to each other as in a wedge or prism, as shown in FIG. 5c. In this example, the volume change is linear with distance along the array in the direction of surface inclination while in the orthogonal direction along a row of holes, the hole length, and thus volume, is constant. In accordance with another alternate embodiment of the invention, an array can be fabricated from a contiguous series of planar surfaces inclined to each other in either one- or two-dimensions such that the through-hole volume is different in both directions along the array. In yet a further embodiment, an array is fabricated from a non-planar surface 54 such as a surface of hemispherical curvature as shown in FIG. 5d.

Figure 6:
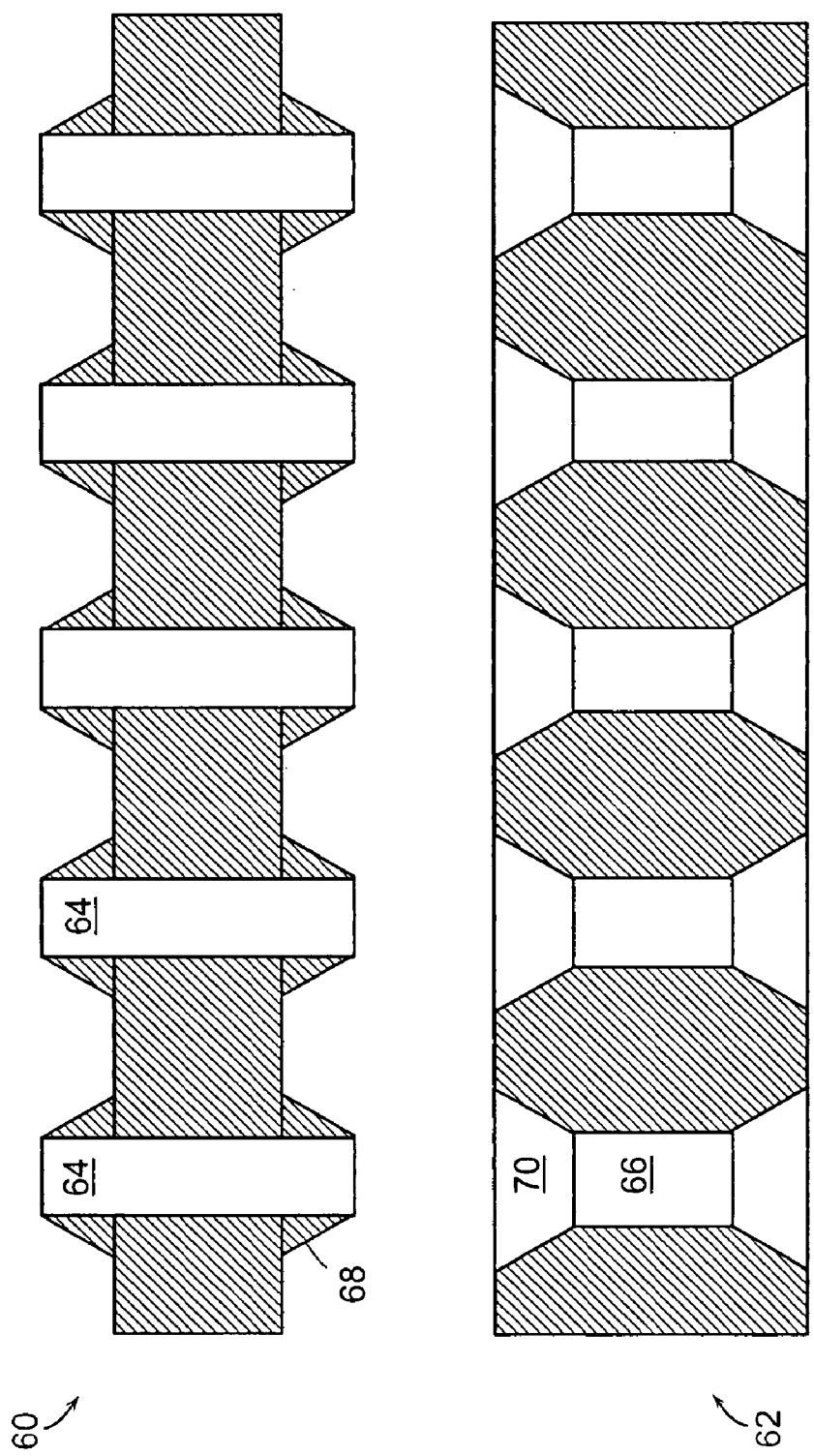
FIG. 6 shows an example of an interlocking array.

For each array geometry, a second array fabricated having surfaces that are the complement of the first array's geometry may be used, in accordance with alternate embodiments of the invention, to facilitates vertical stacking of the arrays, as shown in FIG. 6. Alignment of through-holes 64 of plate 60 with through-holes 66 of plate 62 is provided by inserting protruding segments 68 into corresponding indentations 70. Other array geometries with greater than four-fold rotation symmetry with respect to the array surface normal will facilitate interlocked and self-aligned stacking of arrays with matching positive and negative geometries, within the scope of the present invention. This geometrical arrangement may advantageously obviate the need for alignment pins which are typically required for registration of stacked planar arrays.

Applications of Arrays of Non-Uniform Volume

One application of arrays having through-holes of non-uniform volume is mixing of different volumes of liquids such as in a dilution sequence, as described below. An advantage of this method is that stacking of multiple arrays, as also described below, may be obviated while a wide range of dilution may be achieved.

Another application of arrays of either constant or non-uniform through-hole volumes is fraction collection from chromatographic elution. The through-hole array advantageously provides the ability to collect a large number of small volume fractions, which can then be further separated within the through-hole array, as described below. This, in turn, advantageously increases the resolution of chromatographic separation over prior technology.

Figure 5F:
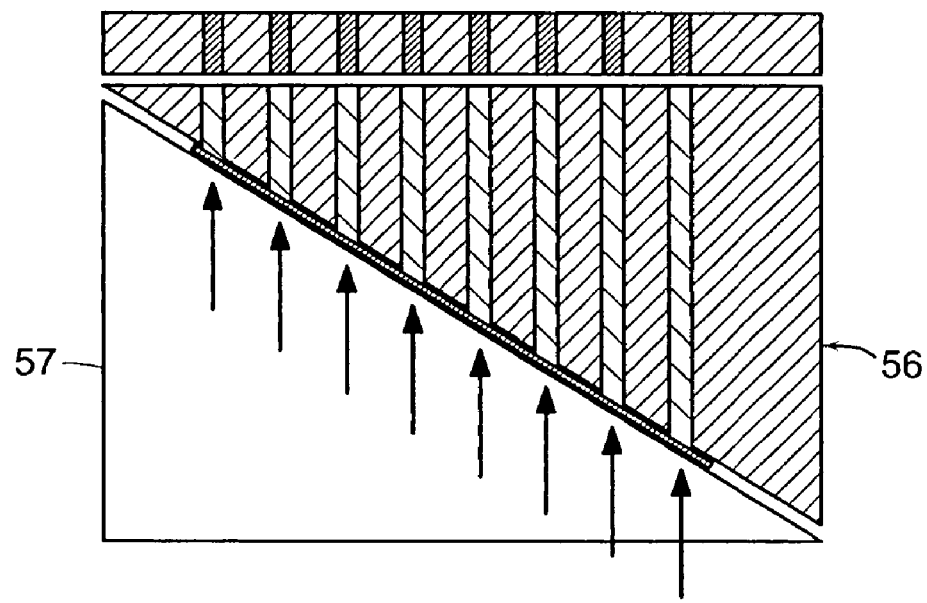

Yet another application of non-standard array geometries is for massively parallel liquid chromatography or electrophoresis. More particularly, referring to FIG. 5e, a through-hole plate 56 is employed whose thickness increases in one lateral direction (such that the plate has the shape of a prism) resulting in a linear increase in hole length with array position. A second through-hole prism 57 is brought together with the first prism 56 along their common hypotenuse 58 thereby producing an array of through-holes 12 of substantially equal length. To use this structure as a liquid chromatography column, each hole is filled with a porous gel 55 characteristic of liquid chromatography. The sample 51 to be analyzed is applied to one end of the array, as from a sample plate 53, for example, and a pressure is applied to drive fluid sample 51 through each hole. Each component in the mixture will travel at a different velocity through the gel matrix resulting in a separation of the mixture along the column length. For example, small molecules will move rapidly through the channel to its opposite end, whereas, after the same duration of time, larger molecules may typically have traveled only a fraction of that distance. The intersection of each through-hole with the hypotenuse along which the prisms are joined corresponds to different travel lengths along the chromatographic column. Separation of the array into its constituent prisms, as depicted in FIG. 5f, gives a "snapshot" of the mixture components distributed as a function of array position. Rather than a function of time, the chromatograph is transformed into a function of position by running identical samples in an array of columns with a known inter-column delay, expressed either as a time, or, equivalently, as a length. By sequentially analyzing the material output from each through-hole along the direction of increasing plate thickness, an equivalent chromatograph can be reconstructed. Further mixture separation is possible if the gel porosity is made different in the array direction orthogonal to the wedge orientation. Decreasing gel porosity further increases the retention time for each component, thus leading to finer resolution of the mixture components. Electrophoretic separation may be achieved in an analogous manner, where an applied electric field is the driving force.

Fabrication of the Through-Hole Array

Figure 7:
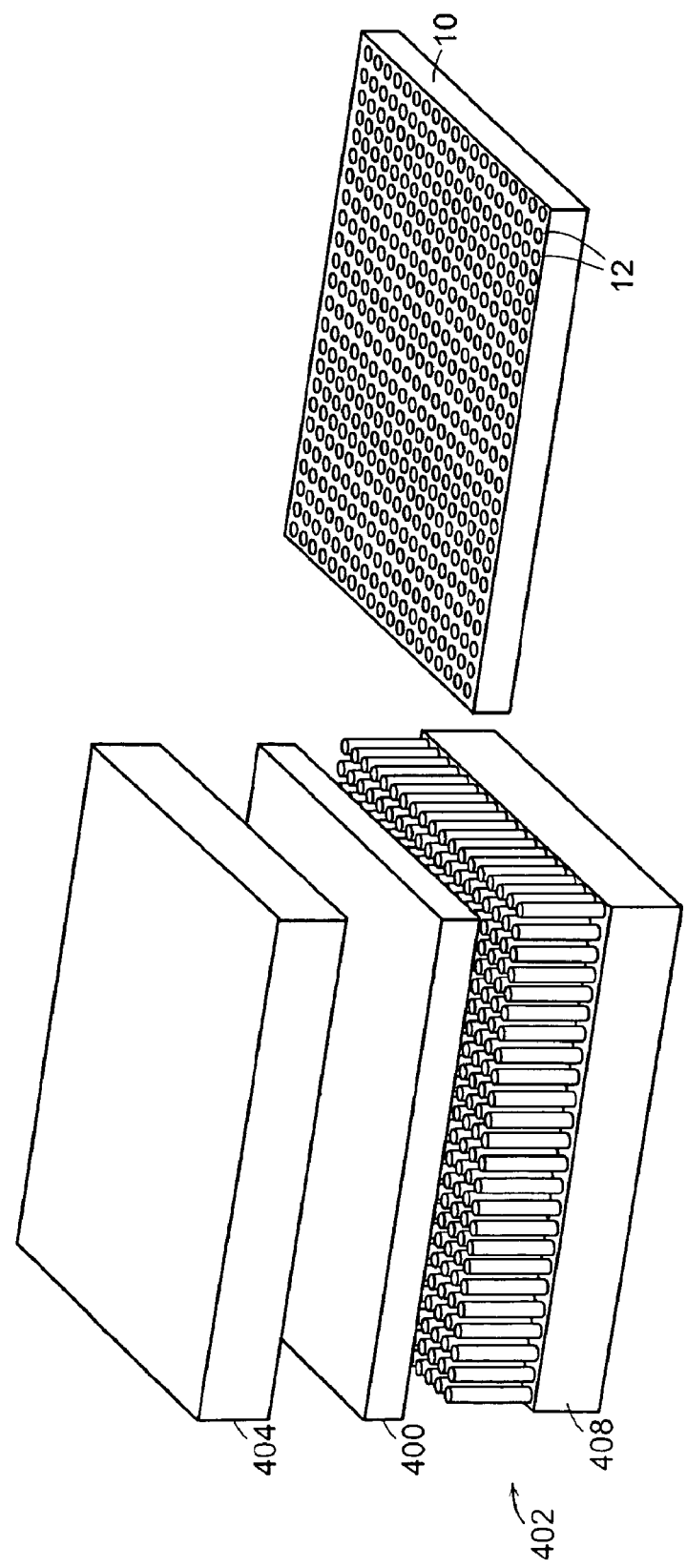
FIG. 7 depicts the configuration of a compression mold for compression molding on an array of through-holes in accordance with an embodiment of the present invention.

Referring now to FIG. 7, through-holes 12 may be formed in platen 10 by any of a variety of means appropriate to the material of platen 10. Through-hole forming methods include, by way of example, laser ablation by means of an ultraviolet (UV) excimer laser which may form 100 μm through-holes in glasses and polymers. Additional through-hole forming techniques include mechanical drilling, electrochemical methods such as micro-electrical spark discharge machining (EDM), employing radio-frequency pulses for ionizing removal of conductive materials, or, in accordance with other embodiments of the invention, by selective chemical or charged-particle etching techniques. Additionally, microcapillary bundles of glass fibers of varying compositions may be drawn from preform and sliced to form platens, and then selectively etched to form through-holes.

As shown in FIG. 7, through-holes 12 may be formed, in materials such as thermoplastics or polycarbide, by punching platen blank 400 using punch array 402 and die array 404, in conjunction with a high-pressure ram. Punching pins 406 may be formed in punch block 408 using microwire EDM, as described in detain in the following discussion, or by micro-etching techniques such as chemical or charged-particle etching. Additionally, punch array 402 may be formed using microsawing techniques. Die array 404 is similarly formed using microfabrication techniques known in the manufacturing arts.

High-density arrays of through-holes may be formed in conducting materials, including conductive ($>10\Omega^{-1}$–$cm^{-1}$) silicon wafers, using a combination of wire and die sink EDM. EDM is typically used in the preparation of tooling dies for injection molding. As is well known, the machining process involves ionizing away the surface of a conducting material, typically a metal. EDM-can be performed using a tip-based electrode, or a "wire." Wire-EDM is used when fine surface finishes are required, or when subtle machining features not achievable with a tip electrode are desired. Traditional wire-EDM machining utilizes wire approximately 250 μm in diameter. Due to the small dimensions and high packing densities of the invention an adapted microwire EMD process is used that employs wires with diameters down to 30 μM. This system may provide surface finishes down to 100 nm, essentially a mirror finish.

Figure 8:
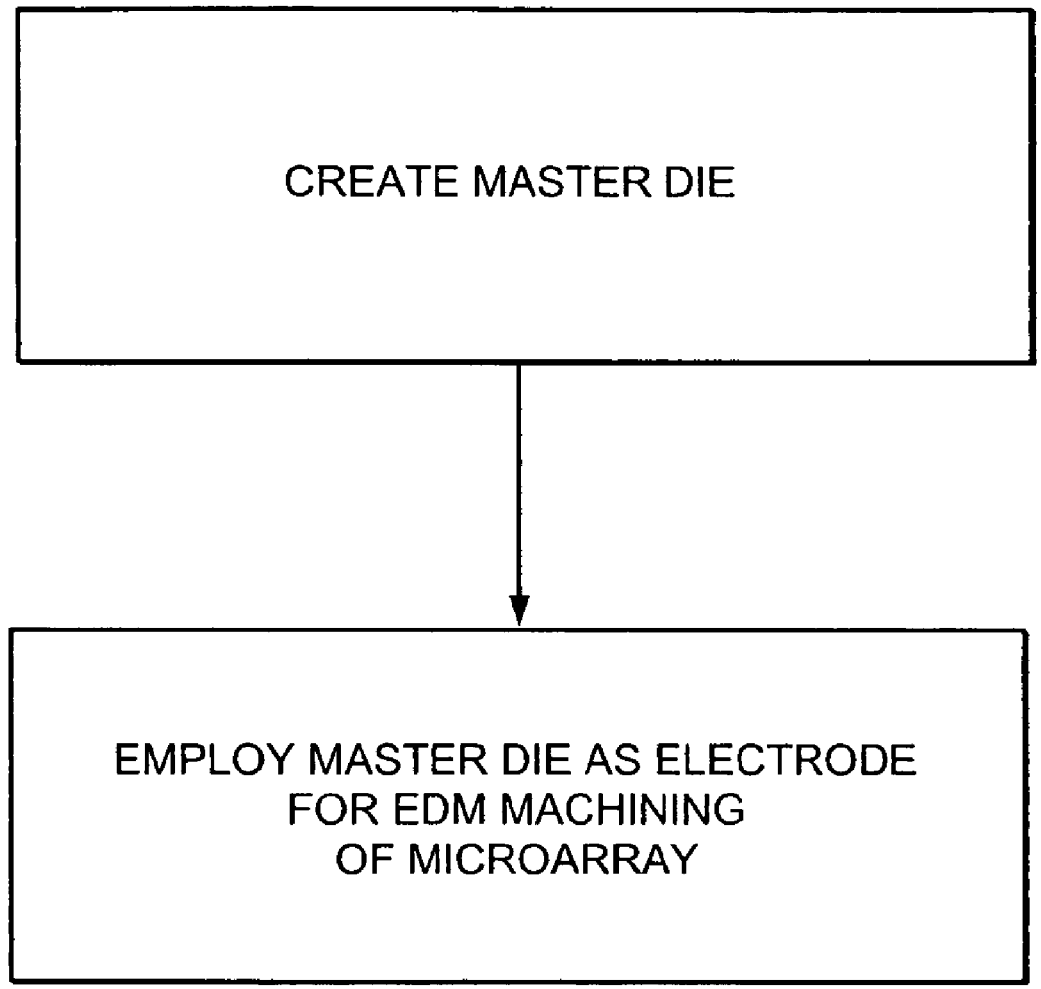
FIG. 8 is a flow chart depicting steps in the fabrication of a through-hole array by EDM, in accordance with an embodiment of the invention.

Referring to FIG. 8, a typical method for preparing a through-hole array using microEDM machining follows a two-step process. The first step is the creation of a positive or master die. The second step uses another EDM machine called a "sink-EDM." The sink-EDM machine uses the master as an electrode and thereby creates a negative copy in the machined conducting material. This negative copy is the resulting microarray. The master electrode can produce multiple negatives before needing to be replaced, thereby increasing manufacturing throughput for production of the chips.

In contrast with deep reactive ion etching—the process commonly used to produce high aspect ratio structures in silicon—the EDM technique described herein may advantageously reduce fabrication time and cost.

After the master die is fabricated with wire EDM, it may typically be used to sink an array of microchannels through a 0.5-mm thick silicon wafer in less than two minutes. Additional machining time, during which the master die moves largely in the plane of the array, is typically needed to enlarge the holes to the desired dimension and to improve the surface finish. The fabrication process described has been used to sink microchannels of sizes up to 10 000 elements with cross-sections <300 μm×300 μm and element spacings <500 μm. Another advantage of this technique is that it may also be used to a manufacture stainless steel precision alignment jig that is used to align the chips for mixing and optical readout, as described herein.

Combined with the precision alignment jig, this EDM process results in <10 μm center-to-center total error in channel spacing across the entire array. This guarantees accurate hole alignment across arrays, and when combined with the hydrophobic exterior coating, minimizes cross talk between microchannels.

Referring again to FIG. 7, the master die 408 produced from the process outlined above can be used to create the through-hole arrays from a plastic blank 400. In this approach the die is used as a type of punch to create the through-hole array from a solid piece of plastic. Unlike a punch, however, the master does not force its way through the plastic. Instead, by having the appropriate kinetic energy as it impacts the plastic it essentially vaporizes the solid plastic into low molecular weight gases (with some residual energy dissipated as heat). In this manner the master can be removed from the resulting through-holes without having melted into it. A slight taper on the protrusions of the master that forms the channels facilitates removal of the master from the chip. This process is similar to that which is used in the manufacturing of DVD's, except the manufacture of microwell arrays typically requires significantly greater penetration depths (up to 1 mm deep). Alternatively, plastic microwell plates may be manufactured by injection molding of metal masters formed by EDM.

As discussed above, with reference to FIG. 1b, it is desirable to prevent cross-communication between the various through-holes during loading and other operations by coating the surfaces of the platen with a hydrophobic coating 22. It is also desirable to coat the inner surfaces of the through-holes with a hydrophilic coating 24 so that they retain fluids. In accordance with embodiment s of the invention, the inner coating 24 may be chemically blocked to prevent non-specific binding or derivatized with affinity ligands.

In accordance with preferred embodiments of the invention, a dense array 10 of through-holes 12 is produced in silicon and coated in silicon oxide by oxidation. The surfaces of the conductive silicon are covered in a thin oxide layer. The wafer is then cleaned by soaking in a mixture of hydrogen peroxide and sulfuric acid, or other caustic solvent cleaning solution, to remove organic materials. Clean silicon oxide thus produced has a high surface energy. The top and bottom faces of the arrays are made hydrophobic by exposing them to vapor from a solution containing an appropriate silanizing agent (such as polydimethylsiloxane, sold as Glassclad 216™ by United Chemical Technologies, Inc.) in a volatile solvent. The silanizing agent reacts with the hydroxyl and silanol groups on the array surface and creates covalent bonds to hydrophobic alkyl groups.

The resulting coated arrays can be uniformly loaded with aqueous solutions by simply dipping the array into it. The liquid instantaneously fills the channels through capillary pressure, but does not wet the other surfaces. Hydrophobic coatings produced in this way are stable under high humidity and they can be used repeatedly over several days. Other surface chemistries may be exploited to attach hydrophobic chemical groups to the faces of arrays made from other materials. For example a gold-coated surface reacts with alkane thiols to attach a hydrophobic alkyl groups, as discussed by C. D. Bain et al., *J. Am. Chem. Soc.*, vol. 111, pp. 321-325 (1989), which reference is incorporated herein by reference.

In accordance with other embodiments of the present invention, the surface chemistry of the array faces may also be selectively modified by substituting other silanizing agents for the polydimethylsiloxane telomer. This method may advantageously prevent aqueous solutions from adhering to array faces during array loading and also act as physical barriers between the aqueous solutions in adjacent through-holes. During this process a positive pressure of inert gas is applied to the opposite side of the array. The positive pressure within the through-holes prevents the silanizing vapor from reaching the interior surfaces. This method advantageously allows removal and reaplication of the hydrophobic coating.

Array Loading Techniques

Dip Loading

Figure 9C:
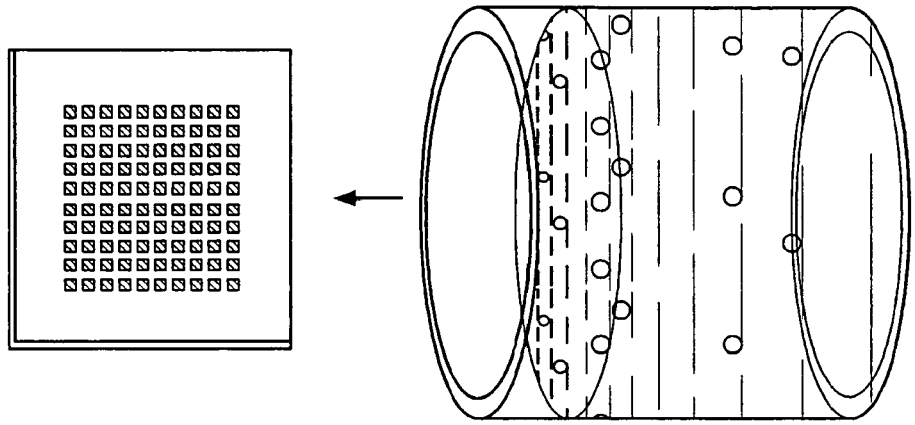
FIGS. 9a-9c depict a sequence of operations for filling a through-hole array with a first liquid.
Figure 9B:
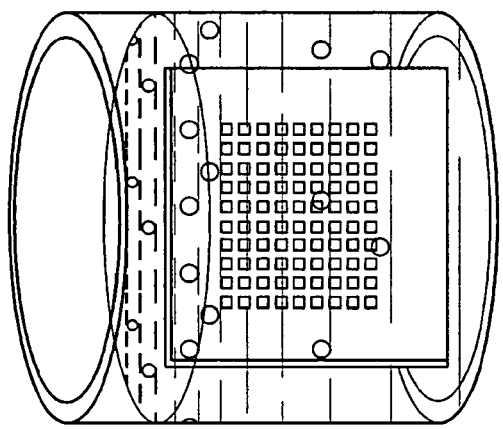
Figure 9A:
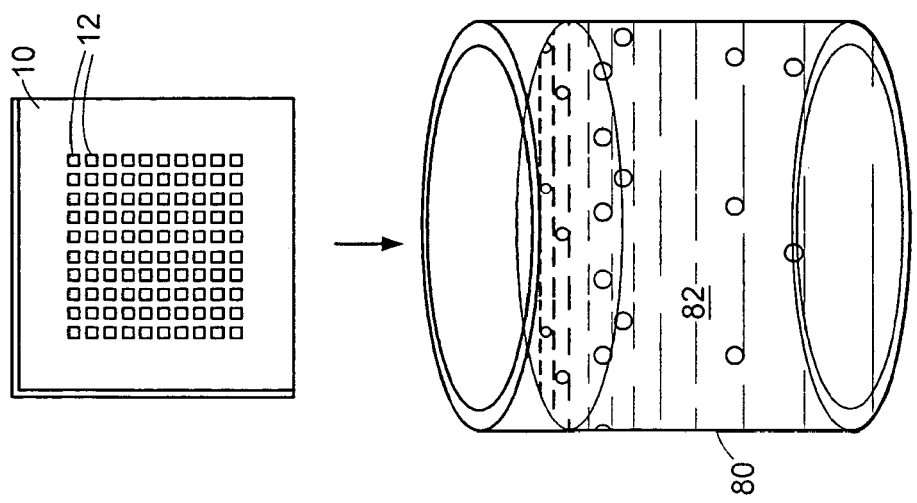

Referring now to FIGS. 9a-9c, array 10 of through-holes 12 may be filled using techniques either that directly address particular through-holes, or techniques that fill the entirety of the array according to a specified pattern based on composition, concentration of a substance, etc.

Dip loading may be employed, for example, in order to fill an entire array with the same solution. A through-hole array 10 is produced and chemically treated to make the array faces hydrophobic and the through-hole surfaces hydrophilic. Plate 10 with through-holes 12 is first lowered into a container 90 containing a first liquid 82, as shown in FIG. 9a. Once plate 10 is fully immersed in the first liquid, it is shaken so that first liquid 82 displaces the air in each of the through-holes, and all the through-holes 12 are filled with first liquid 82. All means of replacing the air in the through-holes is within the scope of the present invention, whether by shaking, applying a vacuum to one side of plate 10, employing electrostatic forces, tilting the plate so that the air is displaced by virtue of its buoyancy, all cited as examples and without limitation, or else by other means. After through-holes 12 have been filled, plate 10 is withdrawn from first liquid 82, as shown in FIG. 9c. The array is typically withdrawn slowly such that the surface of the fluid in the reservoir pulls excess liquid off of the non-wetting array surface. Alternatively the array may be filled with water by spraying the array with water or by sonicating the array in a reservoir of water in order to remove trapped air bubble prior to dip loading. In this case, less agitation is required to uniformly fill the array with solution.

Both convection and diffusion can be used to induce mixing between fluids in microchannel arrays. This can be demonstrated by filling a microarray with aqueous solution of blue dye and by submerging the microarray into a beaker of still water to induce dilution via diffusion. A small mechanical disturbance (such as a tap to the side of the beaker) causes rapid replacement of the blue dye by water. Alternative methods for filling the array with water include spraying the array with water or sonicating the array in a reservoir of water in order to remove trapped air bubble prior to dip loading are also within the scope of the present invention.

Similarly, an array having hydrophilic faces and hydrophobic through-holes may be uniformly filled with a low surface tension liquid such as an alkane.

Loading by Dragging Droplet Along Array Surface

Droplet dragging is performed to load an entire array or a group of channels within a single array with the same fluid. It is appropriate for loading samples which must be conserved because of cost or availability. To perform a loading operation by dragging, a droplet of the loading solution is formed on the end of a syringe needle, micropipette or other fluid dispensing capillary. The drop is placed on the array face over the through-holes to be filled. The capillary is then moved to drag the drop across the surface of the array and over the channels to be filled. Surface tension maintains contact between the capillary tip and the fluid drop. When the drop is depleted additional fluid is dispensed until all desired through-holes have been filled. The capillary and any remaining fluid in the drop are then withdrawn from the array surface. FIG. 1D depicts the loading of a platen 10 with a liquid transfer device 40 in accordance with one embodiment of the invention.

Transfer of Liquids Between Microtiter Plates to Through-Hole Array

In accordance with further embodiments of the invention, a method is provided to transfer liquids from standard microtiter plate formats (96-, 384-, or 1536-wells, for example) to a single array of through-holes or multiple, vertically stacked arrays in which holes in the same spatial location from one array to the next are co-registered. As used herein, the term "registration" refers to aligning a through-hole plate with at least one other through-hole plate, such that the tops of a plurality of through-holes of one of the plates coincide with the bottoms of a plurality of corresponding through-holes of the other plate or plates, thereby creating a plurality of contiguous channels.

All of the filling examples given can be performed in parallel on a single array stack with multiple capillary tubing arrays filled with liquids from different microtiter plates or the same microtiter plate. Fluid may be transferred from chemical libraries stored in 96- and 384-well microtiter plates quite rapidly with these methods. For example, if 100 arrays with $10^5$ through-holes per array are to be filled with liquid stored in 96 well plates, and if each transfer operation (plate exchange, fluid loading and transfer) takes approximately 20 s, then the requisite arrays may be filled within approximately six hours. The filling operations take place preferably in an environmentally-controlled chamber (temperature, humidity, atmosphere, etc.), as described below.

Transfer of Liquids from Microtiter Plates to One or More Through-Hole Array

Figure 10:
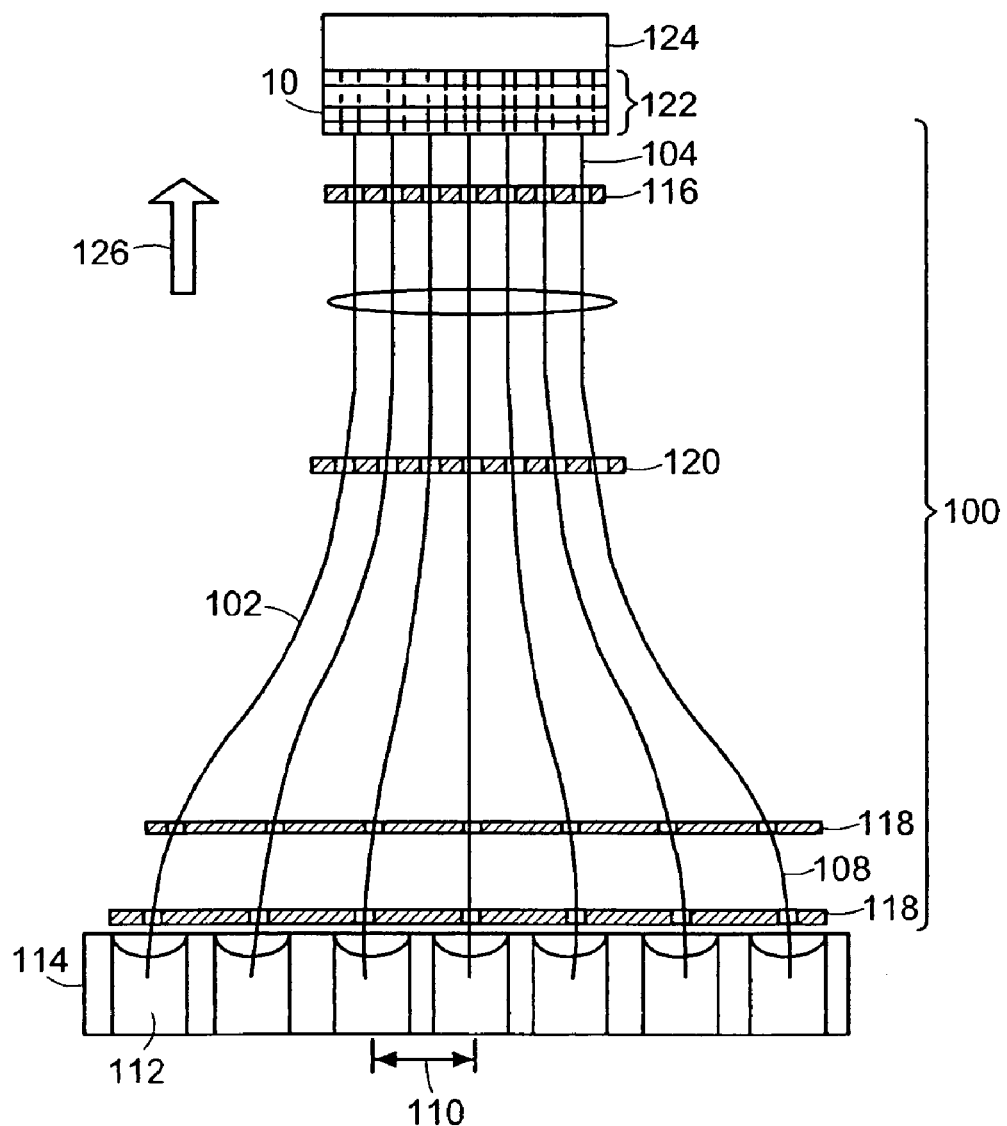
FIG. 10 is a schematic depiction of a method for sampling the contents of a large-format microtiter plate and loading a subarray of the through-hole array in accordance with an embodiment of the present invention.
Figure 11:
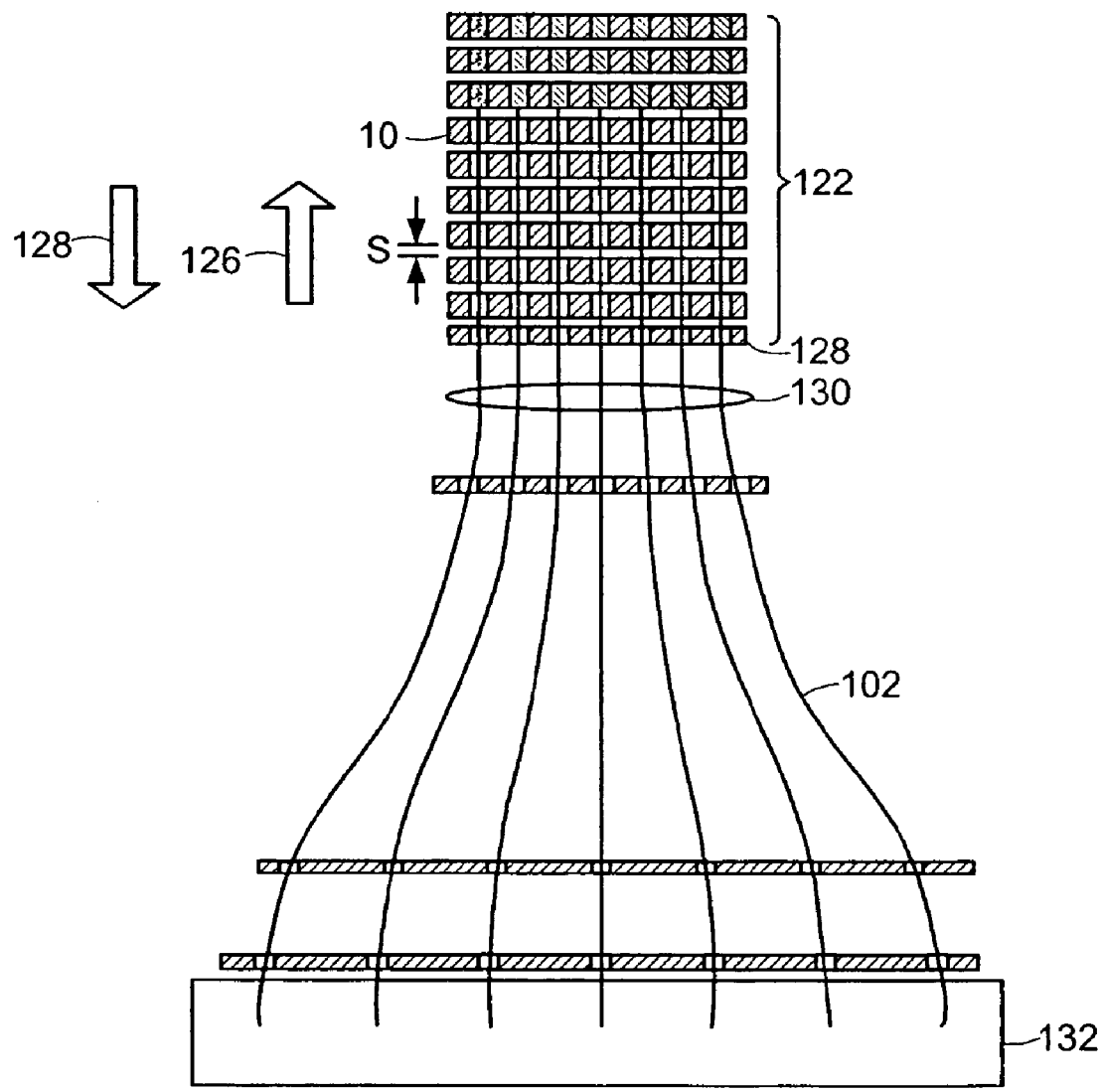
FIG. 11 is a schematic depiction of a method for sampling the contents of a large-format microtiter plate and loading subarrays of multiple through-hole arrays in accordance with an embodiment of the present invention.

Referring now to FIGS. 10 and 11, further embodiments of the invention provide an apparatus and methods that are particularly suited to the transfer of liquids from standard microtiter plate formats (such as 96-, 384-, or 1,536-well formats) to a single array of through-holes or multiple, vertically stacked arrays in which holes in the same spatial location from one array to the next are co-registered Producing such stacks of arrays may be employed advantageously for producing replicates of molecular or cellular libraries.

Capillary Tube Array

Viewed in cross-section, a capillary tube array 100 is constructed from capillary tubing 102 with an external diameter that fits precisely into the through-holes of a through-hole microwell array 10. Tubing array 100 is designed such that tubing 102 at one end 104 has a center-to-center spacing 106 equal to the spacing between holes in through-hole array 10 (or, alternatively, to an integral multiple of the inter-hole spacing) and tubing at the opposite end 108 has a center-to-center spacing equal to the center-to-center spacing 110 of wells 112 in a microtiter plate 114. Plates 116, 118, and 120, with through-holes having these and intermediate separations serve as jigs to hold the tubing in a regular array. Additional through-hole plates 116, 118, and 120 placed between the two ends may advantageously serve as spacer jigs providing additional support for the tubing array as the center-to-center spacing varies over the tubing length.

In addition to filling a single through-hole microwell array 10, the technique depicted in FIG. 10 may be advantageously employed for filling an entire stack 122 of hole-registered microwell arrays. The internal volume of each tube 102 in the capillary array 100 is slightly greater than the total volume of a column of aligned holes in the array stack 122. For example, if the through-hole dimensions in the array are 250 µm×1000 µm, giving a volume per through-hole equal to 62.5 nl, then the volume of one set of holes in a stack of 100 arrays is 6.25 µl (100×.62.5 nl). Capillary tubing with an internal diameter of 200 µm and an external diameter of 245 µm is readily available; thus a minimum tube length of 200 mm stores the volume of fluid needed to fill this set of through-holes.

One end 108 of tubing array 100 is inserted into the wells of a microtiter plate 114, each tube being inserted into a corresponding well 112. Next, a negative pressure difference is applied across the length of tubing 102 to draw liquid, in direction 126, from each well into its corresponding tube. Negative pressure could be applied to each tube individually, or as shown in FIG. 10, the ends of the tube array can terminate in a chamber 124 that can be partially evacuated. After filing each tube of the array, the microtiter plate 114 is removed. The liquid can be stored in the tubing array for an indefinite period of time, either frozen or in a humidified environment. It can also be readily transported to another location in this format. Multiple tubing arrays can be filled from the same microtiter plate (assuming there is sufficient volume of liquid per well) or different tubing arrays can be filled from different microtiter plates.

Proximity Filling

Embodiments of the invention also provide for methods for filling a stack of arrays, as shown in cross-section in FIG. 11, by bringing the end of a tubing array 130 into close proximity with a matching set of through-holes in the array stack 122. The tubing array can be aligned relative to the array stack by an alignment plate 128 with through-holes having the same center-to-center spacing as the through-holes into which fluid is placed. Each array 10 in the stack 122 is spaced a small distance s that may be, but is not limited to, an equal distance to the through-hole spacing. Application of pressure to the end of the tubing array, placed inside a pressurized container 132, forces fluid from each capillary tube 102 into the opposing through-hole. After the through-hole is filled, a liquid drop can begin to grow in the space between the two plates. When the drop reaches a size that it contacts the through-hole in the plate above it, surface tension draws some fluid into the through-hole. Once the fluidic bridge is established, liquid can flow into the through-hole, driven by the constant pressure applied to the opposite end of the tubing array. With no applied pressure, the drop retreats into the through-hole, the fluidic bridge between each plate is broken, and the separation of array plates after filling can be facilitated (i.e., because there is generally no surface tension that needs to be overcome). Successive filled plates 10 are then withdrawn, and the tube array may be retracted in direction 128. Each vertically registered set of through-holes may thus act as a channel for fluid flow. The hydrophobic coatings on the exterior surface of the arrays prevent liquid from flowing into adjacent holes. This technique can also advantageously be used to create replica plates of a cell library by applying a cell suspension with a pressure uniformly to the array stack.

Inter-Hole Spacing Matched to a Microtiter Plate

Figure 12A:
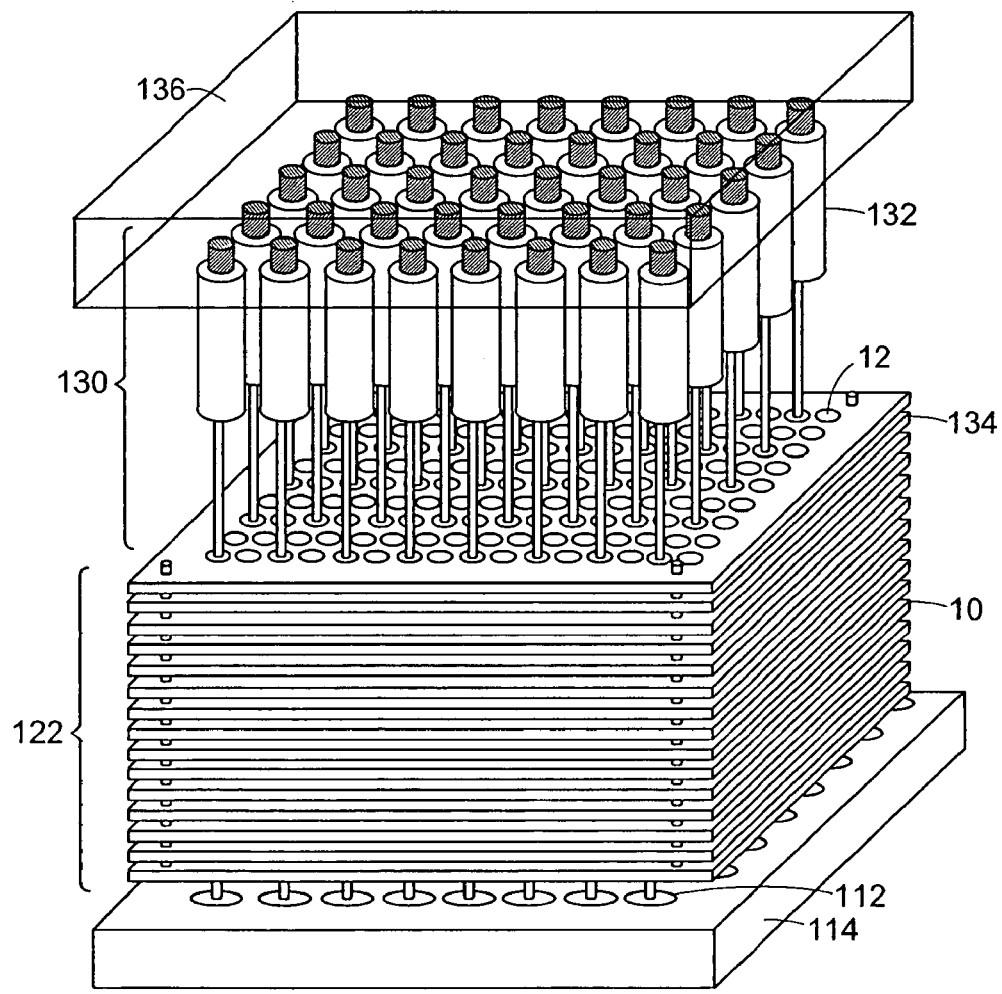
FIG. 12*a* depicts parallel loading of subarrays of multiple stacked microwell arrays in accordance with embodiments of the present invention.

A method for filling a through-hole array stack, in accordance with alternate embodiments of the invention, is shown in FIG. 12. This method uses a through-hole array 10 having the same lateral dimensions as a microtiter plate 114 and having a hole spacing that is an integral fraction of the well spacing in the microtiter plate 114. When the array is placed on top of the plate, one or more through-holes 12 align with respect to each well 112 in microtiter plate 114. An array 130 of syringes 132 with a center-to-center spacing equal to the well spacing can thus be positioned over a stack of through-holes registered with respect to each other and the microtiter plate. The syringe array is inserted through a through-hole plate 134, such that the plate is a mechanical guide for the syringe tubing as it is moved relative to the array stack. The syringe plungers are mechanically coupled and actuated by a mechanical or electromechanical driver module 136, such that liquid is drawn into or expelled from each syringe in parallel. The syringe tubing outside diameter is preferably sized relative to the through-hole lateral dimensions to give a sliding fit, and the tubing can have a length suitable to allow insertion through the array stack 122 and into the liquid contained in the microtiter plate wells 112.

The volume of liquid withdrawn into each syringe preferably equals the volume of liquid in a column of aligned through-holes in the array stack. The liquid can then be dispensed as the syringe array is retracted from the array stack, and the rate of dispensing can be synchronized with the rate of withdrawal, such that each through-hole addressed by the syringe array is filled. Once this operation is completed, either a new set of holes in the array stack can be filled from the same microtiter plate or the syringe array can be washed and different set of holes filled from a different microtiter plate.

All of the filling examples given above may be performed in parallel on a single array stack with multiple capillary tubing arrays filled with liquids from different microtiter plates or the same microtiter plate. The time to transfer fluid from chemical libraries stored in 96 and 384 well microtiter plates with these methods can be quite rapid. Assuming, for example, that 100 arrays with 10,000 through-holes per array are to be filled with liquid stored in 96 well plates, and that each transfer operation (plate exchange, fluid loading and transfer) takes approximately 20 seconds, then it would take approximately six hours to fill all of the arrays. The filling operations can take place in an environmental controlled chamber (temperature, humidity, atmosphere, etc.). The invention also provides a method for screening compound libraries to predict the ability of each compound to be absorbed by a patient.

Transfer from a Microtiter Plate with an Array of Flexible Members

Figure 12C:
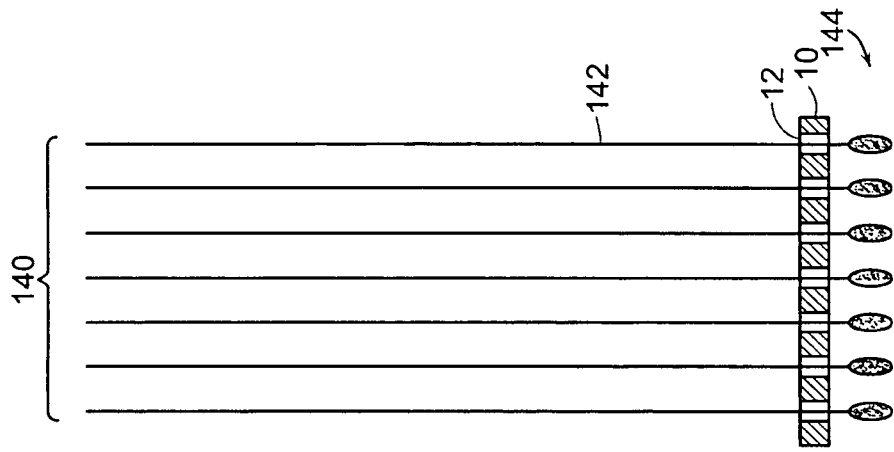
FIGS. 12*b* and 12*c* depict parallel loading of subarrays of a microwell array by means of flexible members, in accordance with embodiments of the present invention.
Figure 12B:
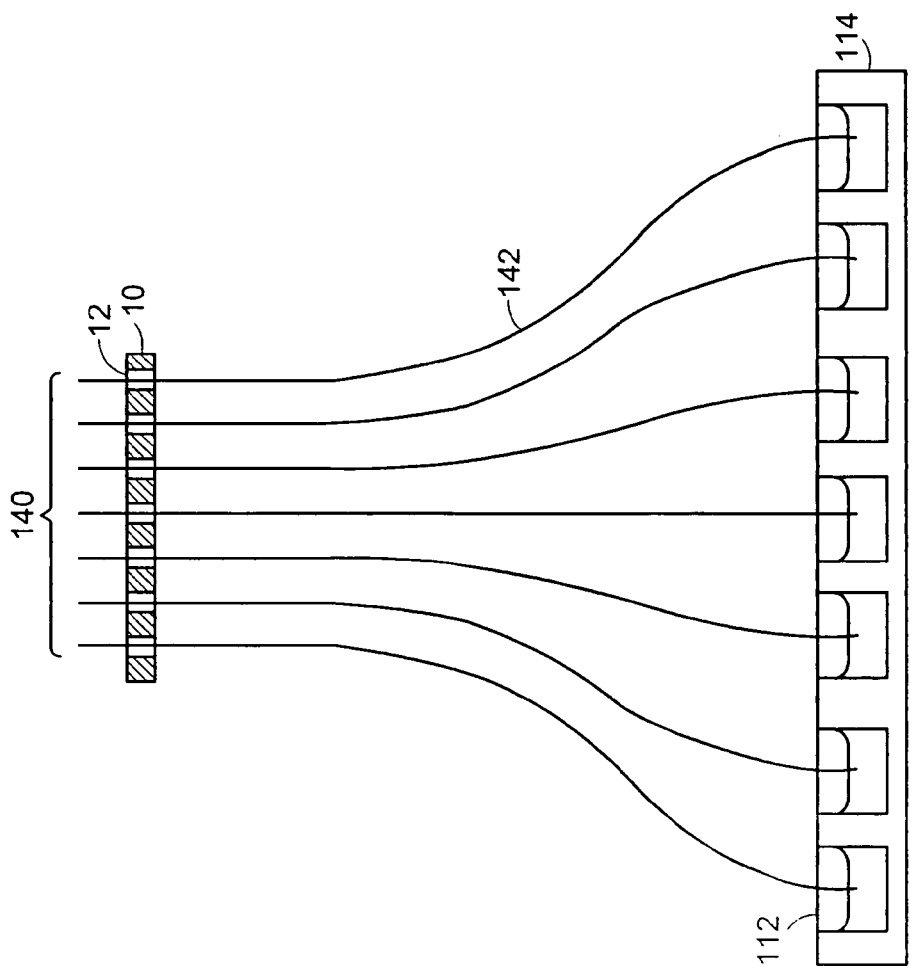

As now described with reference to FIGS. 12b and 12c, fluid can be transferred from individual wells 112 of a microtiter plate 114 with an array 140 of flexible members 142, e.g., shape memory alloy fibers. The fiber diameter is equal to or less than the inside dimension of the through-holes 12 in the array 10 into which fluid will be transferred. The number of fibers in the bundle may, for example, be equal to the number of wells in the microtiter plate 114. The ends of the fibers at one end of the bundle can have a center-to-center spacing equal to the spacing of the holes in the through-hole array, while the ends of the fibers at the opposite end can have a center-to-center spacing equal to the spacing of wells in the microtiter plate. The fibers can be held in place with a series of through-hole jigs designed to increase the spacing between fibers from one end of the bundle to another. Once fixed in place, shape memory alloy fibers can be heated above their critical transition temperature to make the imposed fiber curvature permanent. After they are cooled to room temperature, the fibers can be removed from the holding jig, with the change in fiber center-to-center spacing intact. The close packed end of the fiber bundle can then be inserted into the through-hole array into which fluid from each well in the plate is to be placed. The opposite end can be arranged such that each fiber is positioned above a well in the microtiter plate, and the ends of the fibers can be immersed in the fluid contained in each well. On retraction of the fiber bundle from the microtiter plate, as shown in FIG. 12c, a small volume drop 144 remains attached (e.g., by surface tension) to the end of each fiber 142. A force may be applied to the opposite end of the fiber bundle to pull the bundle through the holes 12 of the through-hole array 10, such that the fluid is brought into contact with the corresponding through-holes. As the fibers 142 are pulled through the hole 12, surface tension acts to hold the liquid in the through-hole as the fiber is removed.

Successive Dilution

Figure 13:
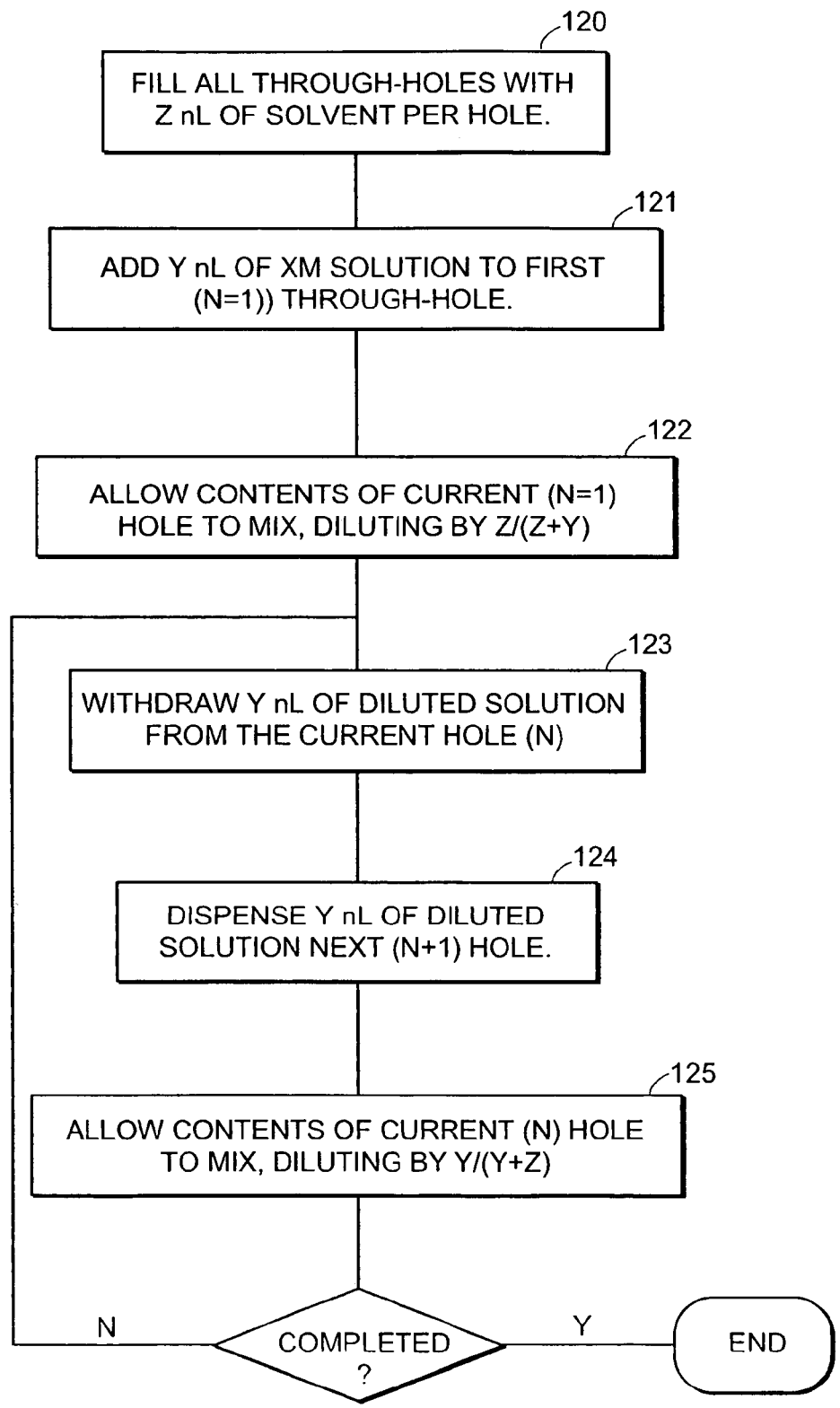
FIG. 13 is a flow chart depicting a method for successive dilution of the contents of a microwell array in accordance with an embodiment of the present invention.

Addressable loading may also be employed to fill a series of through-holes with different and specified concentrations of the same solute. A chosen series of through-holes is filled with a quantity of solvent, denoted Z nanoliters (nL), either by dipping the holes into the solvent or by dispensing the solvent from a microsyringe 232 (shown in FIG. 21), or other fluid transfer device. This is shown as the first step 120 in the flow chart of FIG. 13. In step 121, microsyringe 232, or another fluid transfer device, is filled with an X molar solution of the solute, and is then positioned over the first through-hole. Y nL of this solution, where (Y+Z) nL is sufficient volume to overfill the hole and to create positive menisci, is expelled such that it forms a droplet at the end of the syringe tip. The syringe tip is lowered until the solvent droplet contacts the surface of the solution, causing the two liquids to mix 122 and produce a solution of concentration YX/(Y+Z) molar. The outer surface of the syringe tip and the faces of the array must be nonwetting toward the solution being dispensed. The syringe plunger is then withdrawn in step 123 to suck up Y nL of the diluted solution. The syringe tip is positioned above the next (N+1) through-hole 124 and Y nL of the diluted solution is dispensed into the solvent to dilute 125 by another factor of Y/(Y+Z). The process is repeated so as to dispense solution into a series of individual through-holes, each time diluting by Y/(Y+Z).

Chemical Gradient Methods

In accordance with preferred embodiments of the invention, a particular chemical species is not loaded uniformly into all the holes of an array, but, rather, a gradient of chemical species is created in at least one dimension in a two-dimensional through-hole array. As used in this description and in any of the appended claims, the term "gradient" refers to its ordinary mathematical meaning, i.e., a variation, along one or more directions, of a specified quantity. The directions, here, are taken along the surface of an array of through-holes. Thus, a gradient in the concentration of a specified chemical species in the through-holes may be said to exist with respect to a particular direction, or, for that matter, with respect to various directions. Thus, a particular gradient may be, but need not be, monotonic, and the concentration of a species, in a specified direction, may rise and fall.

Referring now to FIGS. 9a-9c and 14a-14c, dip loading methods described above may be used for creating a concentration gradient in an array of through-holes. In accordance with such methods, the array is dipped into a chemical solution at a controlled rate such that the chemicals in the solution have different amounts of time to mix with, or react with, substances by diffusion into various through-holes.

Figure 14C:
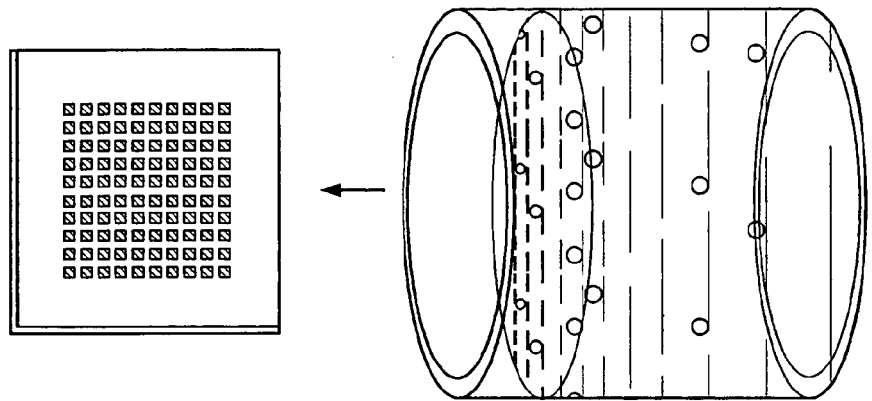
FIGS. 14*a*-14*c* depict a sequence of operations for exposing respective through-holes of a through-hole array to a second liquid and for creating a specified gradient of a specified characteristic with respect to placement of the through-holes in the array in accordance with an embodiment of the present invention.
Figure 14B:
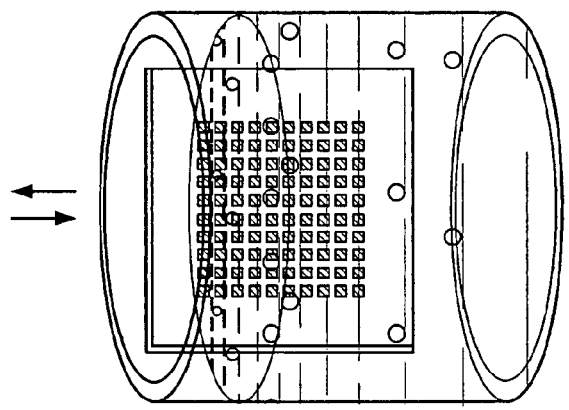
Figure 14A:
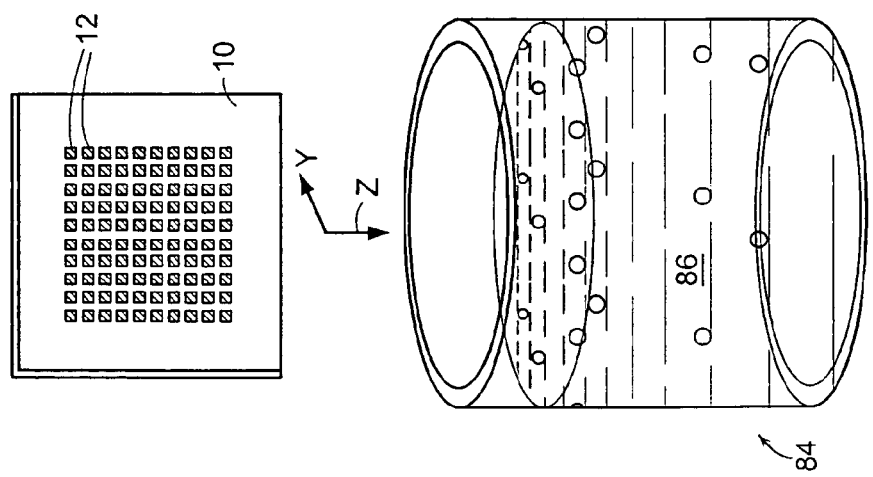

After an array has been filled, by dip loading, with first liquid 82, as discussed above with reference to FIGS. 9a-9c, plate 10 is subsequently lowered into a second container 84 containing a second liquid 86, as shown in FIG. 14a. Since the through-holes of plate 10 are now filled with the first liquid 84, the second liquid 86 may diffuse into, mix with, displace, or otherwise react with, the contents of through-holes 12. Each of these processes is characterized by a rate. Instead of fully immersing the plate until the particular reaction, physical or chemical, runs to completion, plate 10 may be partially immersed into second liquid 86, as shown in FIG. 14b, for a specified duration of time, and then withdrawn, wholly or partially, as shown in FIG. 14c. If plate 10 is reimmersed in liquid 86, to a different depth 88 and for a newly specified duration of time, certain of the through-holes 12 will contain material subject to differential physical or chemical processes. Thus, a gradient will have been created with respect to the direction z along the array of through-holes. Naturally, this process may be repeated or otherwise modified to create a specified gradient.

Figure 14D:
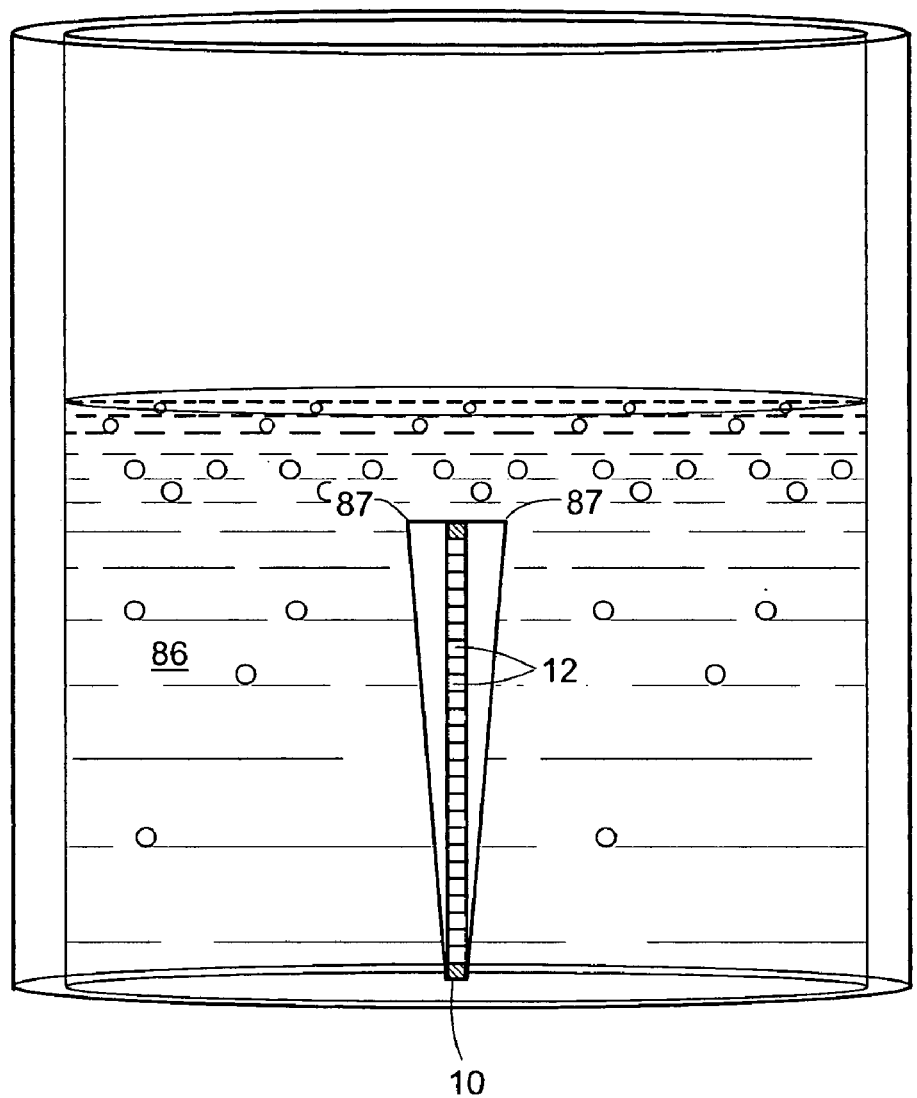
FIG. 14*d* shows a side view is shown of a through-hole array plate with a graduated filter for providing a concentration gradient in accordance with an embodiment of the invention.

In accordance with alternate embodiments of the invention, other means may be employed in order to spatially modulate the concentration of a specified species allowed to diffuse into a through-hole located at a particular position within the array. Referring to FIG. 14d, a side view is shown of through-hole array plate 10 immersed in liquid 86. Diffusion of liquid 86 into through-holes 12 is modulated by membrane or filter 87, for example, that, by virtue of its tapered shape or otherwise, gives rise to a gradient of a specified species with respect to the position of a through-hole within the array.

In a related example, by slowly lowering a through-hole array filled with a gel forming solution thin-edge first into a polymerization initiating mixture different gel densities may be obtained within in holes. By rotating plate 10 by 90° about axis y transverse to the surface of the plate, and then slowly dipping into a reagent that derivatizes the gel with a free cationic moiety, and then rotating another 180° about y and slowly dipping into a reagent that derivatizes the gel with an anionic moiety, a two-dimensional size/charge selection matrix is created that is useful for separating protein mixtures in a manner similar to a 2-D polyacrylamide gel, but with the advantage of greater separation speed and greater access to the separated proteins.

Figure 15:
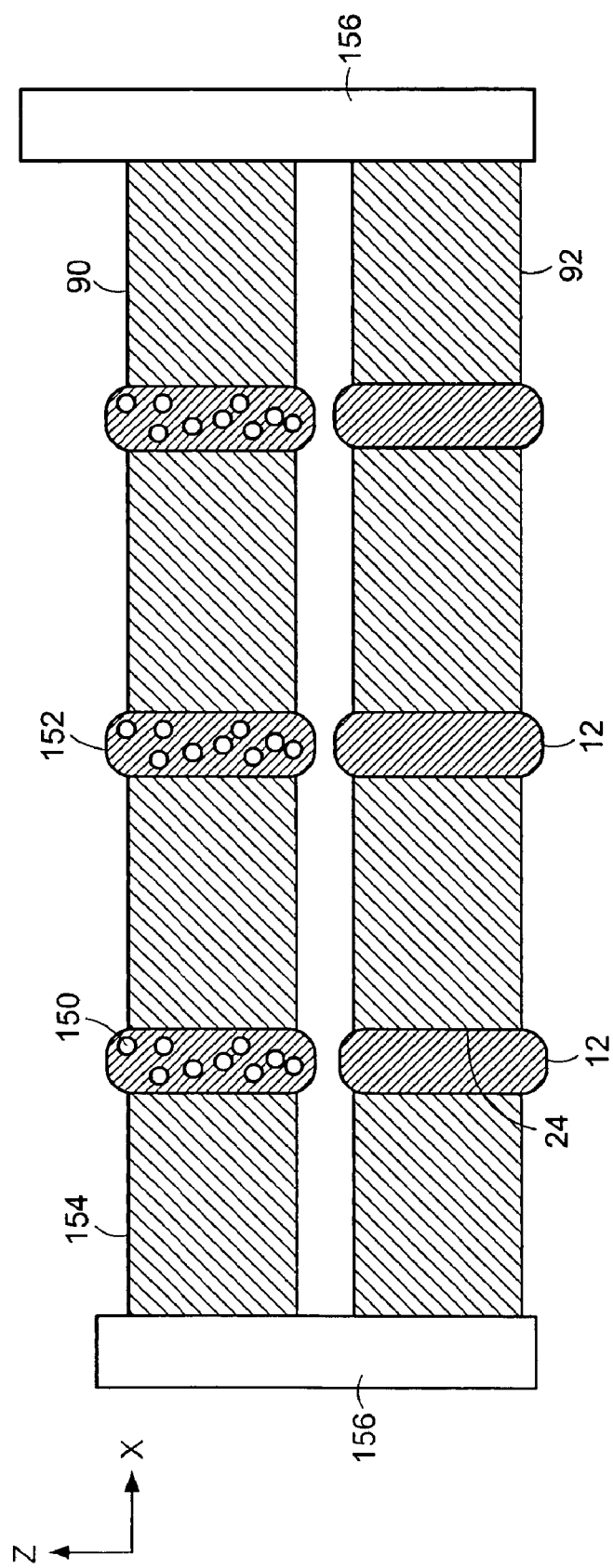
FIG. 15 depicts mixing of the contents of a through-hole array with the contents of another through-hole array brought into registration of the through-holes in accordance with embodiments of the present invention.

In another embodiment, concentration gradients within through-hole arrays are use to optimize the concentrations of A and B in a two-component reaction between Reagent A and Reagent B. The mixing process is described in greater detail below. Referring to FIG. 15, a first through-hole array, shown in cross section and designated generally by numeral 90, is loaded with Reagent A using a chemical gradient method that results in the through-holes along one row, in the x direction, of the array will have the same concentration of A and the concentration gradient is along the array columns, in the z direction. A second array, designated generally by numeral 92, is loaded with Reagent B such that the concentration gradient is along the rows (x direction) of the array and through-holes along a column (z direction) of the array have all the same concentration. Bringing the two arrays in contact causes mixing between aligned through-holes 12. Along each row or column of the combined arrays the concentration of A relative to B in the mixture changes in a regular and known manner. Along the array diagonal, the concentrations of A and B in the mixed liquids are equal and but changing in overall concentration.

Variants from the basic scheme for creating a known two-dimensional gradient in the relative proportions of A and B include loading the A and B arrays by dipping along a diagonal, by the orthogonal combination of two arrays each with a 2-D gradient of A relative to B or by dilution with arrays loaded with Reagent A or B where some of the through-holes are empty. Analysis of the through-hole contents readily determines optimal reaction conditions since the reaction conditions in each through-hole are known. Gradients created in the solution with respect to quantities other than solute concentration are also to be understood to be within the scope of the present invention, and may include, without limitation, such characteristics as temperature, electric field, magnetic field, etc.

Mixing and Dilution

As discussed in greater detail in the following sections, microwell plates may advantageously be stacked for such purposes as mixing or dilution. One such application is the apportionment among through-holes of a sample of cells. Considering, for purposes of example only, through-holes on a single plate that are 250 μm square and 500 μm deep. When three such microchannel plates are stacked (as would be the case in a 2-step assay), the total volume of a single channel (i.e., the combined volume of three through-holes) is ~100 nL. If the entire channel is filled from a dense yeast cell culture (~$10^7$/mL) each channel then contains approximately $10^3$ yeast cells. Based upon a yeast cell volume of 70 $\mu m^3$, the maximum number of cells per 100 nL channel is on the order of $10^6$, consonant with a typical minimum of 100 cells per microchannel is required to compensate for variable yeast cell response to the bioassays.

Referring to FIGS. 15-19, mixing and dilution are shown between the contents of two substantially planar through-holes array plates 90, 92 (i.e., array plates having neither flanges nor indentations). In FIG. 15, in particular, a cross-sectional view is shown of portions of two through-hole arrays 90, 92. Both the top and bottom surfaces of each platen are hydrophobic, as discussed in detail above. The through-hole walls 24 are preferably hydrophilic. Through-holes 12 of both platens are overfilled with high surface energy fluids 150, such as aqueous solutions, for example, such that each through-hole 12 has a positively-curved meniscus 152 protruding above the platen surface 154.

Alternatively, the platen surfaces 154 may be hydrophilic and a sufficient amount of a low surface energy fluid, such as an alkane, for example, is loaded into the through-holes 12 to form positive menisci 152.

Figure 16:
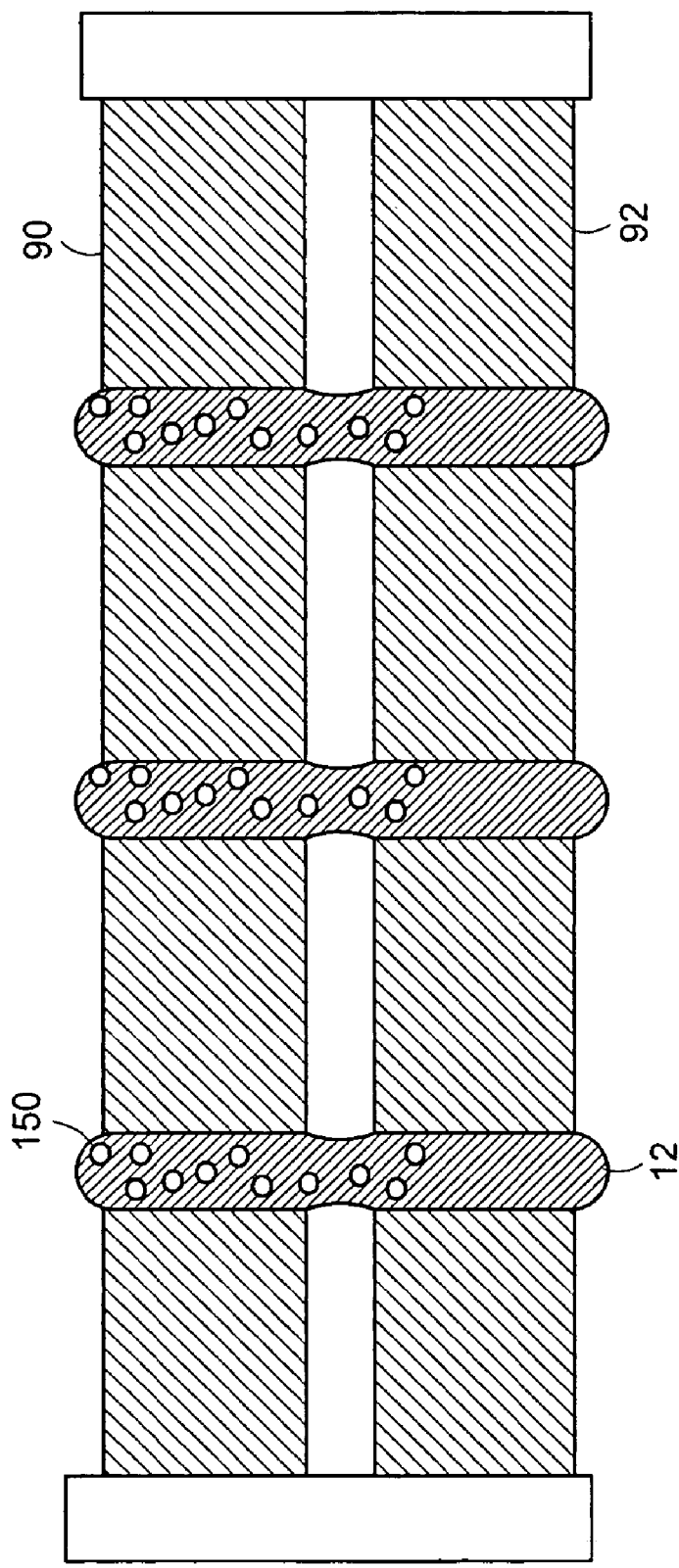
FIGS. 16 and 17 depict further stages in the mixing of the contents of a through-hole array with the contents of another through-hole array brought into registration of the through-holes in accordance with embodiments of the present invention.
Figure 17:
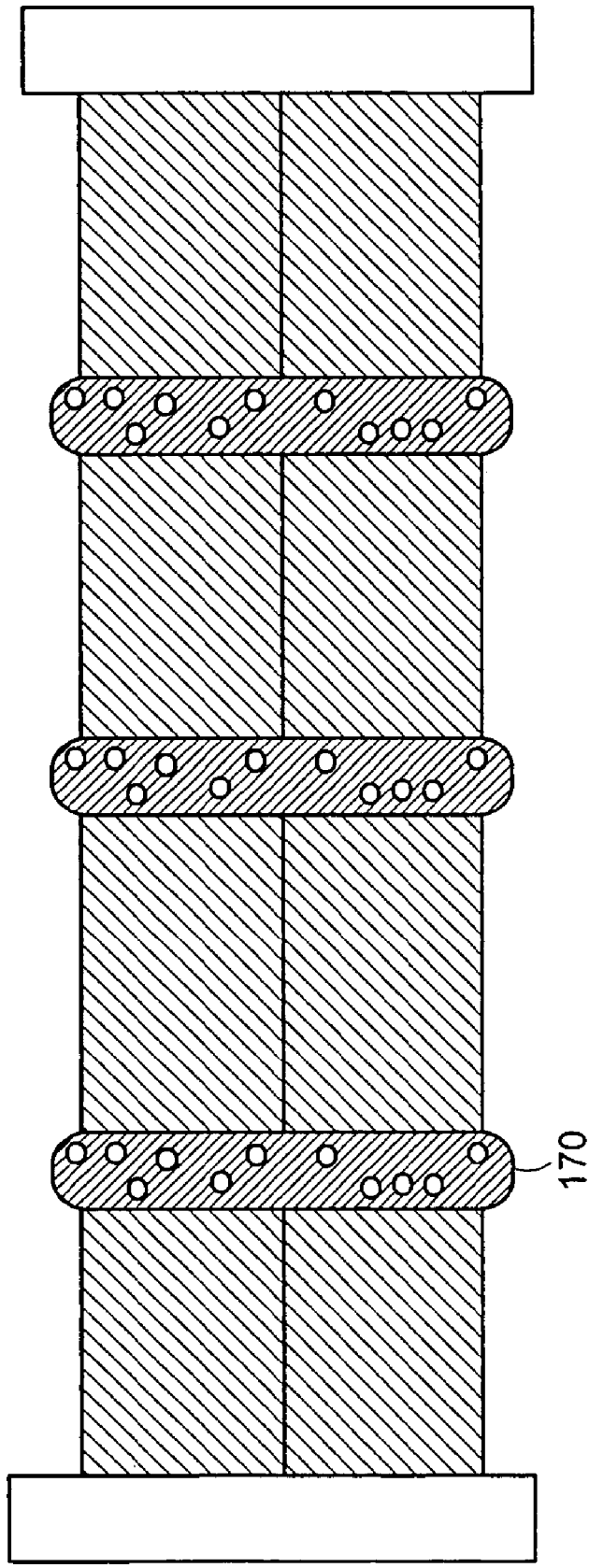

FIG. 16 shows a cross-sectional view of the two platens 90, 92 after the surfaces of the liquids 150 in co-registered through-holes 12 are brought into contact. The release of the surface tension drives convective mixing between fluids contained in the opposite platens 90, 92. Once the two surfaces of the platens themselves have been brought into contact, each set of two-coregistered through-holes forms a longer channel 170, as shown in FIG. 17. Mixing proceeds within the longer channels by a combination of convection and statistical diffusion.

Figure 18:
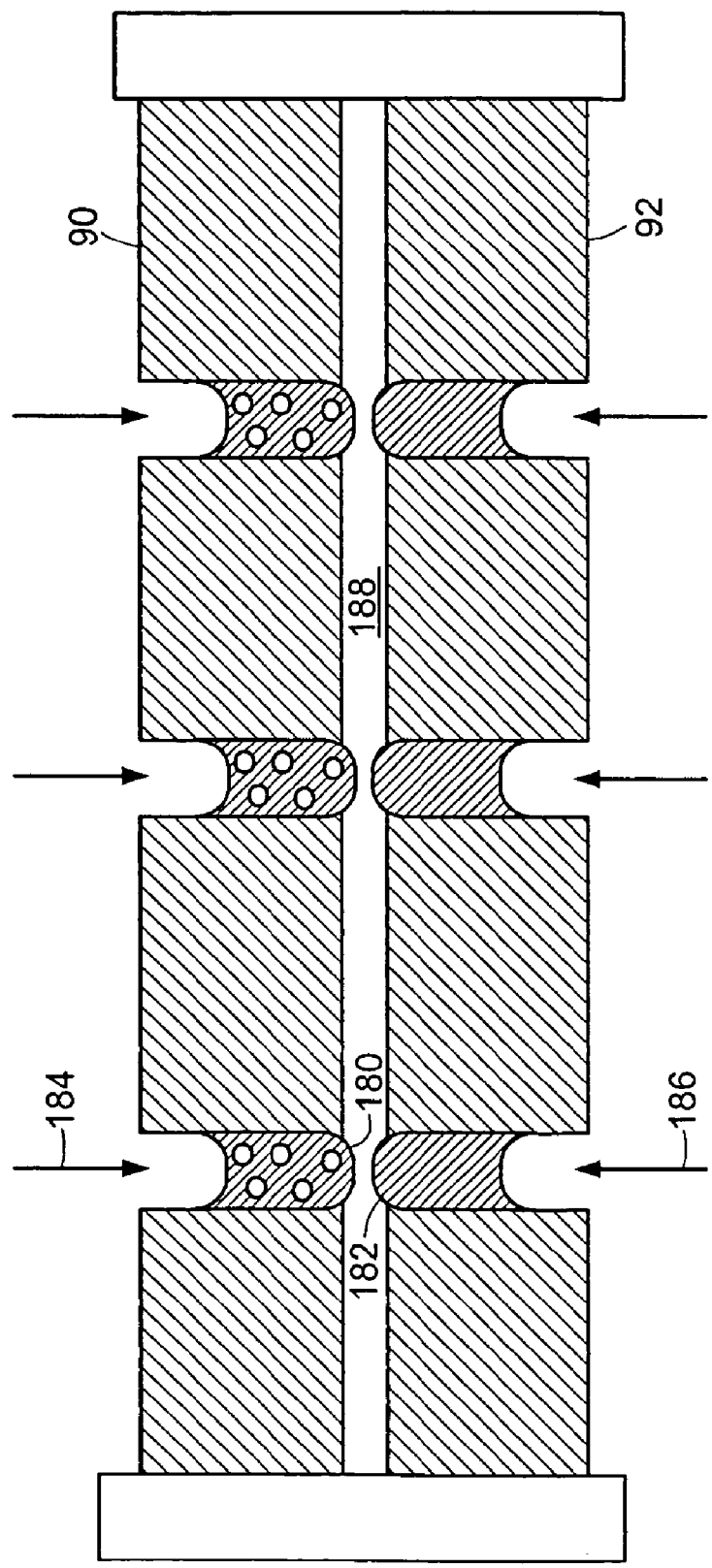
FIG. 18 depicts mixing of the contents of a through-hole array with the contents of another through-hole array by application of external pressure, in accordance with embodiments of the present invention.

Referring to FIG. 18, in cases where through-holes 12 of one or both of arrays 90, 92 are underfilled (such that there is an air-gap separating the fluid 180, 182 when the plates are contacted), the application of slight positive pressure, designated by arrows 184, may be employed to bring the surfaces of the two fluids into contact while a small gap 188 is still present between the surfaces of the two platens 90, 92.

Figure 19:
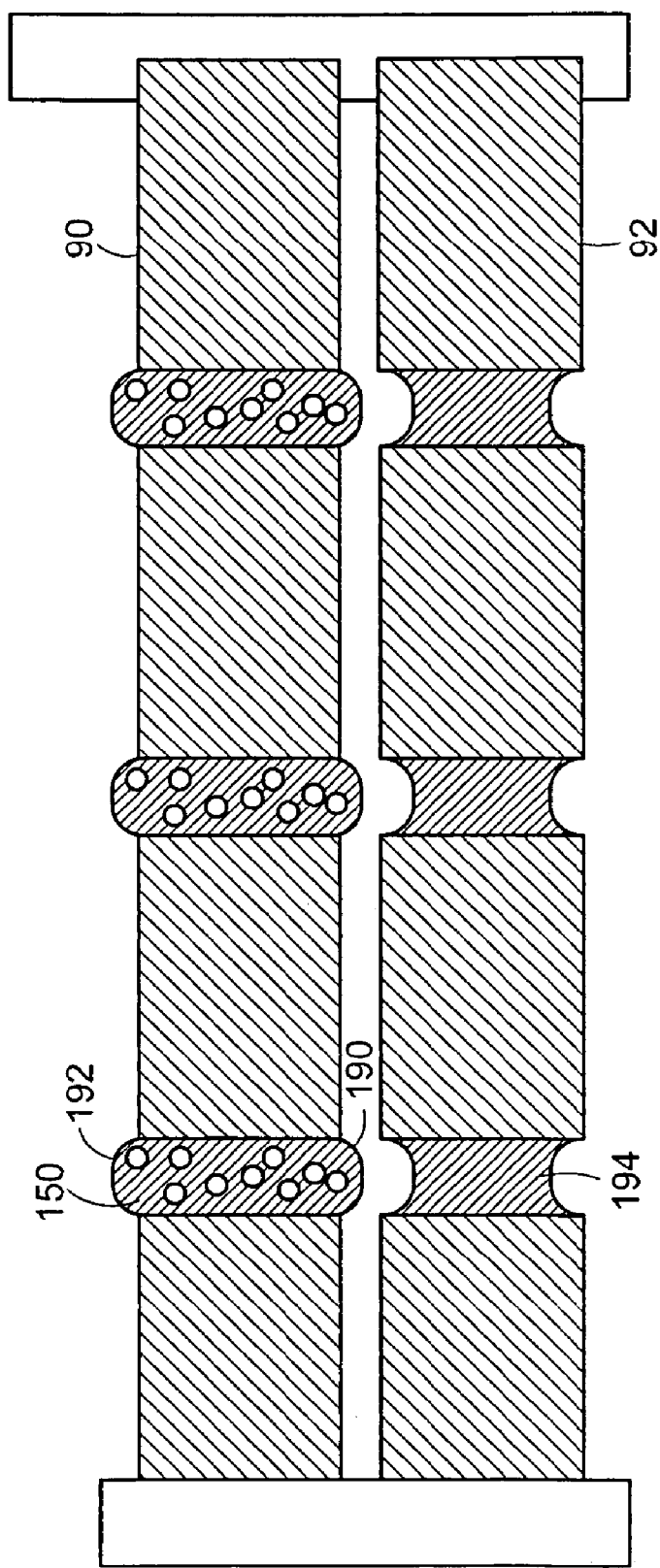
FIG. 19 depicts mixing of the contents of a fully filled through-hole array with the contents of another incompletely filled through-hole array brought into registration of the through-holes in accordance with embodiments of the present invention.

In yet other embodiments of the invention, with reference to FIG. 19, first platen 90 is filled with sufficient fluid 150 to form positive menisci 190, 192, while a second platen 92 is filled with an amount of fluid 194 that is insufficient to form positive menisci, but sufficient to make contact with the surface 190 of the menisci of the first platen when the two platens are stacked. Mixing proceeds by bringing the liquid surfaces into contact as previously described.

Control of Environmental Factors

Figure 20:
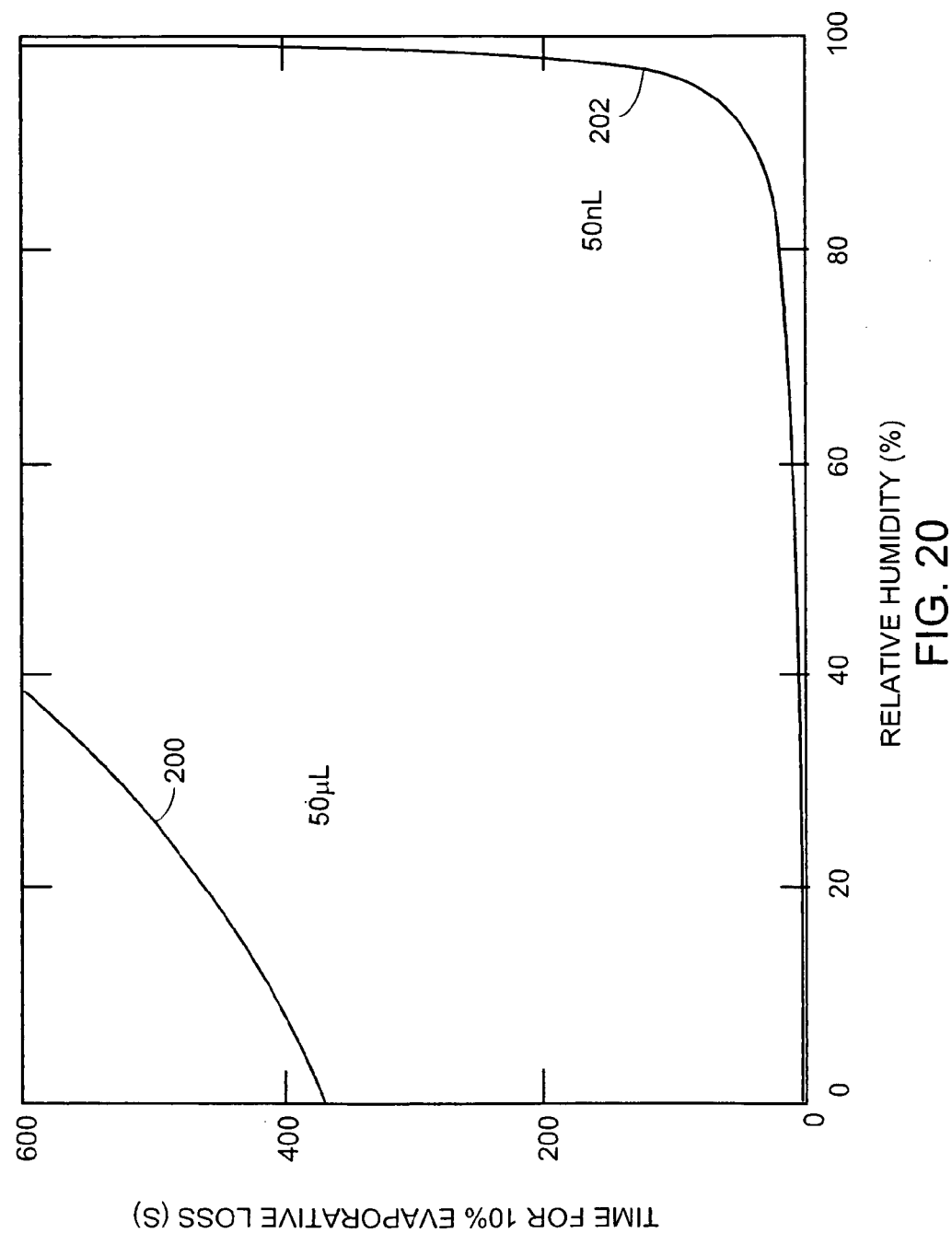
FIG. 20 shows plots of calculated times for evaporation of a water droplet as a function of the ambient relative humidity.

In accordance with embodiments of the invention, methods and apparatus are provided for maintaining high relative humidity levels (typically above 95%) in the environment surrounding through-hole arrays during various operations of the invention. Maintenance of high humidity levels may advantageously minimize, if not eliminate, evaporation of solutions contained in the through-hole arrays. The level of humidity required to keep the volume loss at an acceptable level depends upon the length of time needed to perform the various desired operations, as well as on such factors as the ambient temperature, and the volume of fluid contained in each through-hole. At a temperature of 21° C., the evaporative loss expected from a droplet of water may be predicted in accordance with Fick's law, as depicted in FIG. 20. The time, in seconds, for 10% evaporative loss is plotted for a 50 μL droplet (by curve 200) and for a 50 nL droplet (curve 202) as a function of relative humidity. Unless humidity levels are close to 100%, the smaller droplet will evaporate very rapidly, with a 10% mass loss in 11 seconds at 65% relative humidity.

Humidity Control During Addressable Loading and Unloading

Figure 21:
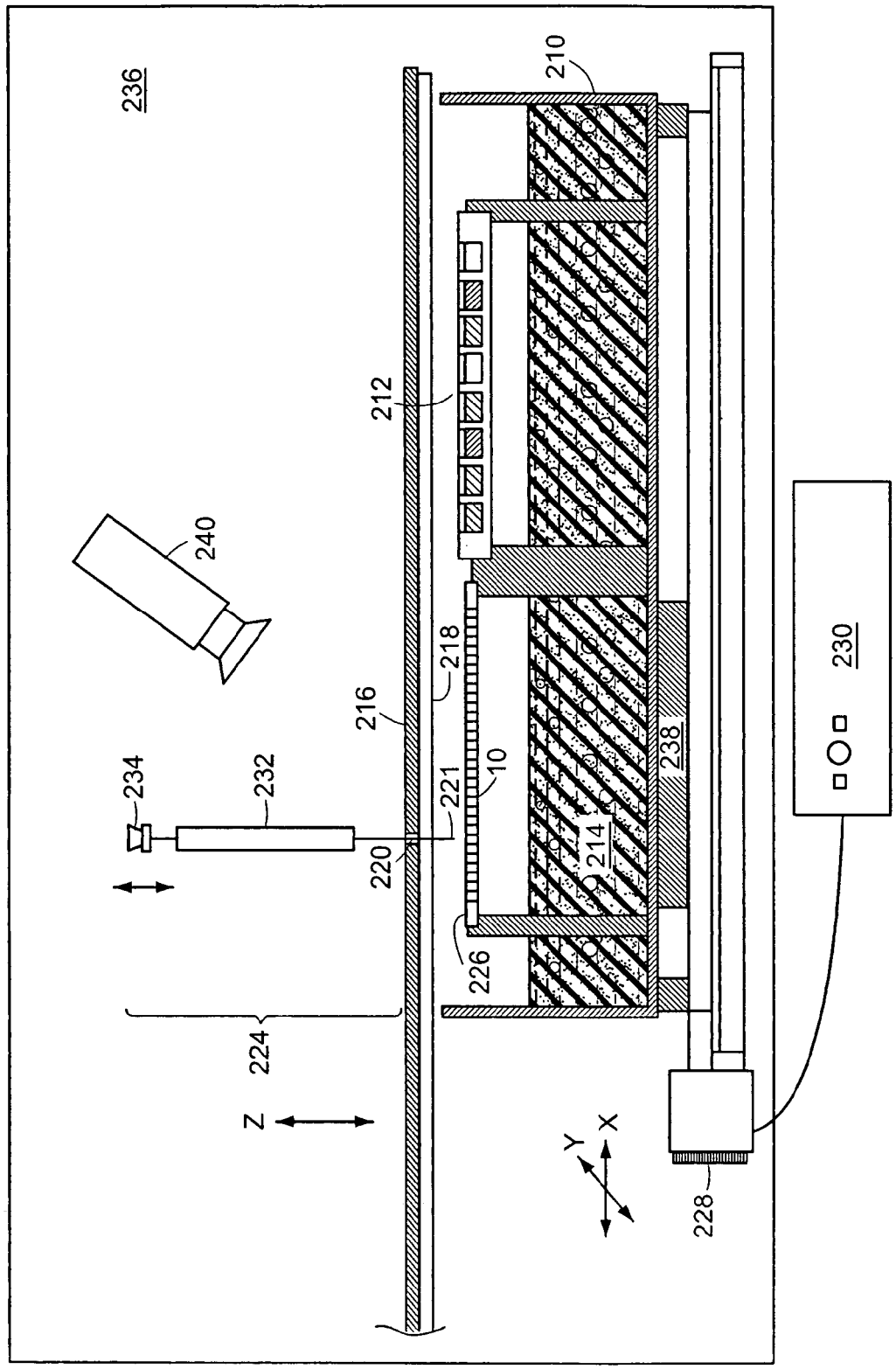
FIG. 21 depicts a humidity chamber for loading and unloading through-holes while maintaining a high relative humidity in the environment surrounding the array, in accordance with an embodiment of the present invention.

With reference to FIG. 21, and apparatus is provided for advantageously reducing the volume of the enclosed environment subject to humidity control. In accordance with embodiments of the invention, a through-hole array 10 is mounted above a reservoir 210 of water. A 96-well, 384-well or higher density microtiter plate 212 is mounted above the same reservoir proximal to the through-hole array. Reservoir 210 may contain a water absorbent material such as a sponge 214 to keep the water from sloshing when the reservoir is moved. An optically transparent plate 216 is placed on top of the reservoir separated from the walls of the reservoir by a thin layer 218 of a viscous non-hydroscopic fluid such as silicone grease, for example. One or more small holes 220 are drilled through transparent plate 216. Through each hole a microsyringe needle 222, microcapillary, pin, cannula, or other fluid transfer element is inserted.

Computer control of motorized translation stages may be provided, such as along axis y to move the fluid transfer element 224 towards and away from the top face 226 of the through-hole array 10. Fluid transfer element 224 may include syringe 232 with plunger 234 fluid transfer element 224, for example. Additionally, the arrays and reservoir may be moved in the plane of the x and y axes, preferably by motorized stage 228 under control of controller 230, with respect to the fluid transfer element. If indicated, further computer-controlled stages may be provided, for example, to actuate the fluid transfer device. Transfer of materials between the microtiter plate and through-hole array proceed by means described above in reference to FIGS. 10-12.

Additional reservoir(s) containing solution(s) for cleaning/sterilizing the fluid transfer element may also be provided within the confines of chamber 236 which encloses the apparatus heretofore described. Alternatively the water in the large reservoir 210 may be used for this purpose. An illumination source 238 may also be provided for to illuminate the array for optical inspection during loading/unloading, either visually or by means of a video camera 240.

Humidity Control During Dip Loading and Mixing

An environment enclosure 236, as shown in FIG. 21, may also be utilized in order to preventing evaporation from the through-hole arrays during dip loading and mixing. Sealable chamber 236 is large enough to contain the array and necessary apparatus for performing such desired operations as are required, including, for example, motors and translation stages 228, as well as an alignment jig 156 (shown in FIG. 15) for mixing operations.

Cool water vapor is generated by an external humidifier and injected into the chamber through a port. An ultrasonic humidifier is able to generate enough vapor to maintain humidity levels above 95% in a 0.13 cubic meter chamber. A circulation system consisting of a fan and baffles is provided to distribute the water vapor uniformly throughout the chamber. Various doors, hatches and iris ports may be provided for accessing the interior of the chamber. The temperature within the box may be controlled by a resistive heater and an electronic temperature controller. Such a chamber may be assembled by attaching a second humidifier to a commercial infant incubator.

Any surface which must be kept dry, including optical windows, and corrodible metals may be heated slightly above the ambient to prevent condensation. A humidity sensor is also provided to monitor humidity levels inside the chamber. All computer and electronic hardware are placed outside the chamber and are connected to components inside the chamber via a wire feedthrough.

The through-hole array may be filled within the chamber, or loaded externally and transferred into to the chamber in a humidified sealed cassette.

Humidity Control During Optical Analysis and Transfer Between Loading Stations

Figure 22A:
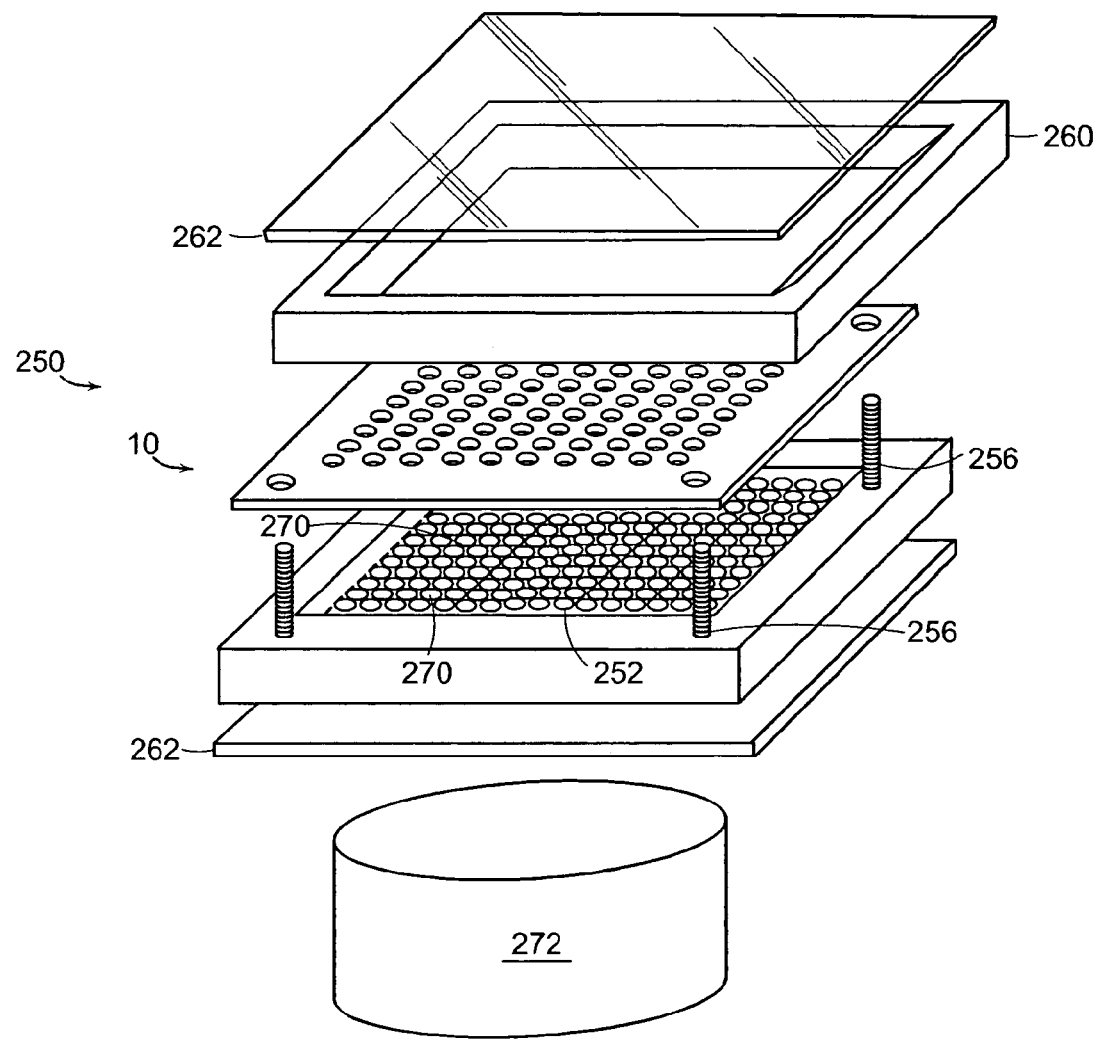
FIG. 22*a* depicts an exploded perspective view of a portable humidity chamber for preventing evaporation of fluid from the arrays during fluorescent imaging analysis, incubation and transferring the array between other humidified environments.
Figure 22B:
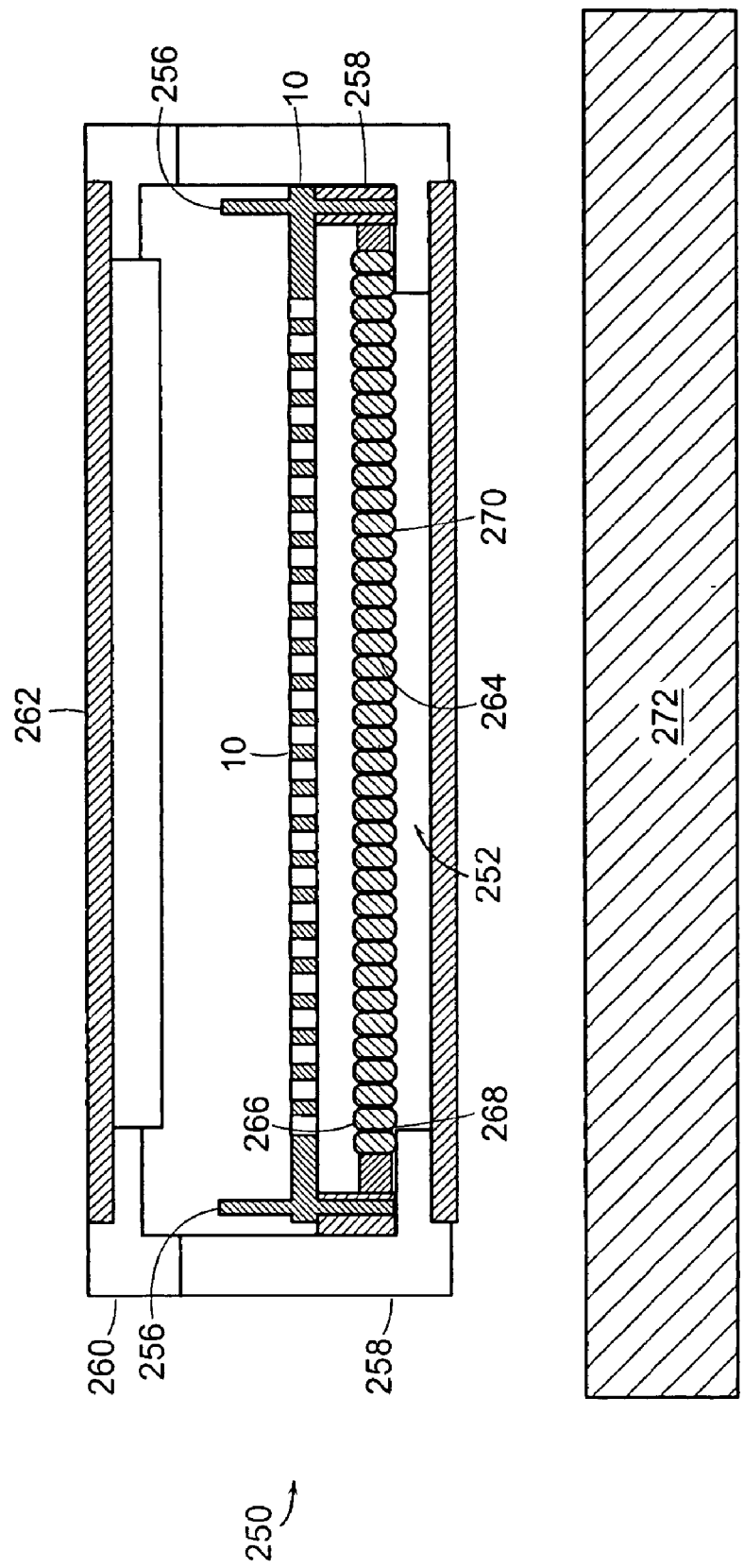
FIG. 22*b* is a cross-sectional side view of the a portable humidity chamber of FIG. 22*a*.

Referring now to FIG. 22a, an exploded perspective view is provided of a compact portable cassette, designated generally by numeral 250, for maintaining relative humidity levels above 95% when the array is removed, for optical analysis, for example, from the humidified loading chamber 236 (shown in FIG. 21). FIG. 22b provides a side view, in cross section, of the humidified cassette 250 of FIG. 22a. Through-hole array 10 and an aqueous microlens array 252 are mounted in a compact, sealable enclosure. The though-hole array is positioned and held in place by means of alignment pins 256 or some other means. Both the array mount 258 and cover holder 260 are covered by an optically transparent plate 262 secured to the mount and cover by adhesive or other mechanical means. The mount may also include magnets, pins, grooves or other physical features to facilitate position the array inside optical analysis equipment.

The humidity is raised by passive evaporation from water contained in a transparent glass microcapillary bundle 252 (or, 'microchannel array') mounted beneath the through-hole array and secured by set screws or some other mechanical means. (Glass microcapillary bundles are manufactured by Schott Fiber Optics, Southbridge, Mass.). Typical dimensions for each capillary 264 are diameter of 200 microns and depth of 1 mm. The top 266 and bottom 268 of the microchannel array 252 are made hydrophobic according to the procedures described above. The arrangement of the capillaries 264 in the array need not be regular. Water 270 in the capillaries forms a set of microlenses which serve to diffuse light from light source 272 across the array and thus provide a uniform illumination field for optical analysis. The use of liquid microlens arrays, generally, is within the scope of the present invention.

Another advantage of the aqueous lens array is that the water is held in place by surface tension. Thus the operator need not keep the humidity cassette level, or avoid applying the typical accelerations that occur when the plate is carried around a room and placed on horizontal surfaces. Also the cassette may be agitated during incubation to promote cell growth inside the arrays.

Control of Other Environmental Factors

Pressure, light and temperature, are controlled by enclosing the array in an appropriately constructed chamber and then controlling the environment inside the chamber by conventional means. To prevent evaporation such chamber must also be equipped to maintain high relative humidity.

Having thus described various illustrative embodiments of the present invention and some of its advantages and optional features, it will be apparent that such embodiments are presented by way of example only and are not by way of limitation. Those skilled in the art could readily devise alternations and improvements on these embodiments, as well as additional embodiments, without departing from the spirit and scope of the invention. All such modifications are within the scope of the invention as claimed.

What is claimed is:

1. An array filling system for transferring liquid to an array of receptacles, the system comprising:
   an array of receptacles characterized by a hydrophilic surface, the receptacles separated by a hydrophobic surface;
   a liquid transfer device capable of holding liquid; and
   a controller configured to position the liquid transfer device in proximity to the hydrophobic surface and to move the liquid transfer device across the hydrophobic surface and over the receptacles to be filled so as to cause sequential communication of liquid in the liquid transfer device with the hydrophilic surface of each receptacle.

2. An array filling system in accordance with claim 1, the system further comprising:
   an array of liquid transfer devices capable of holding liquid,
   wherein the controller is configured to position the array of liquid transfer devices in proximity to the hydrophobic surface and to move the array of liquid transfer devices across the hydrophobic surface and over the receptacles to be filled so as to cause sequential communication of liquids in the array of liquid transfer devices with the hydrophilic surface of each receptacle.

3. An array filling system in accordance with claim 1, wherein the controller is further configured to move the liquid transfer device away from the hydrophobic surface to cause the removal of any excess liquid from the hydrophobic surface.

4. The system of claim 1, wherein the liquid is a test sample.

5. The system of claim 1, wherein a plurality of the receptacles contain a reagent.

6. A method for transferring a liquid into an array of receptacles, each receptacle having a hydrophilic surface, the receptacles separated by a hydrophobic surface, the method comprising:
   a. positioning a liquid transfer device in proximity to the hydrophobic surface; and
   b. moving the liquid fluid transfer device across the hydrophobic surface and over the receptacles to be filled so as to cause sequential communication of liquid in the liquid transfer device with the hydrophilic surface of each receptacle.

7. A method in accordance with claim 6, further comprising:
   c. withdrawing residual liquid from the hydrophobic surface.

8. A method in accordance with claim 6, wherein the step of causing communication of liquid in the liquid transfer device with the hydrophilic surfaces of the plurality of hydrophilic receptacles includes forming a droplet of the liquid on the end of a capillary.

9. A method in accordance with claim 6, wherein the step of causing communication of liquid in the liquid transfer device with hydrophilic surfaces of the plurality of hydrophilic receptacles includes forming a droplet of the liquid on the end of a pipette.

10. A method in accordance with claim 6, wherein the step of causing communication of liquid in the liquid transfer device with hydrophilic surfaces of the plurality of hydrophilic receptacles includes forming a droplet of the liquid on the end of a needle.

11. A method in accordance with claim 6, wherein the step of causing communication of liquid in the liquid transfer device with hydrophilic surfaces of the plurality of hydrophilic receptacles includes transferring liquid into through-holes of an array of through-holes.

12. A method in accordance with claim 6, further comprising:
   c. moving the fluid transfer device away from the hydrophobic surface to cause the removal of any excess liquid from the hydrophobic surface.

13. The method of claim 6, wherein the liquid is a test sample.

14. The method of claim 6, wherein a plurality of the receptacles contain a reagent.

15. A method for loading a liquid into a plurality of through-holes of a platen, the platen having a top surface, the top surface having an opening to each through-hole, the method comprising:
   a. forming a droplet of the liquid on the end of a liquid transfer device;
   b. moving the liquid transfer device so as to drag the droplet across the top surface of the platen and over the through-holes to be filled;
   c. dispensing the liquid in such a manner as to keep the droplet from being depleted; and
   d. withdrawing the droplet from the surface after the through-holes are filled.

16. The method of claim 15, wherein the fluid transfer device is a capillary.

17. The method of claim 15, wherein the platen is characterized by two outer layers of hydrophobic material, and wherein each through-hole has an inner hydrophilic surface.

18. The method of claim 15, wherein the inner hydrophilic surface draws the liquid samples into the through-holes and the outer hydrophobic layers prevent outmigration of the liquid sample.

19. The method of claim 15, wherein the liquid is a test sample.

20. The method of claim 15, wherein a plurality of the receptacles contain a reagent.

* * * * *

UNITED STATES PATENT AND TRADEMARK OFFICE
CERTIFICATE OF CORRECTION

| | | |
|---|---|---|
| PATENT NO. | : 7,547,556 B2 | |
| APPLICATION NO. | : 10/958969 | |
| DATED | : June 16, 2009 | |
| INVENTOR(S) | : Ian Hunter et al. | |

It is certified that error appears in the above-identified patent and that said Letters Patent is hereby corrected as shown below:

On the Title Pg Item (54) in the title of the patent, "FILING" should be replaced with --FILLING--.

FIG. 11 should be replaced with the following drawing, which replaces reference numeral "128" applied to the leftmost directional arrow with reference numeral --127--.

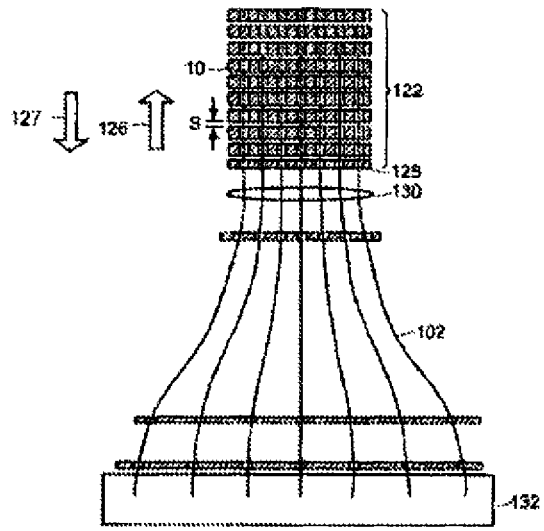

FIG. 11

In column 6, line 63, "enviroment" should be replaced with --environment--.

In column 10, line 60, "reaplication" should be replaced with --reapplication--.

UNITED STATES PATENT AND TRADEMARK OFFICE
CERTIFICATE OF CORRECTION

PATENT NO.        : 7,547,556 B2
APPLICATION NO.   : 10/958969
DATED             : June 16, 2009
INVENTOR(S)       : Ian Hunter et al.

It is certified that error appears in the above-identified patent and that said Letters Patent is hereby corrected as shown below:

In column 13, line 40, reference numeral "128" should be replaced with --127--.

Signed and Sealed this

Twenty-ninth Day of December, 2009

David J. Kappos
*Director of the United States Patent and Trademark Office*

UNITED STATES PATENT AND TRADEMARK OFFICE
CERTIFICATE OF CORRECTION

PATENT NO.       : 7,547,556 B2                                          Page 1 of 1
APPLICATION NO.  : 10/958969
DATED            : June 16, 2009
INVENTOR(S)      : Ian Hunter et al.

It is certified that error appears in the above-identified patent and that said Letters Patent is hereby corrected as shown below:

On the Title Pg Item (54) and at Column 1, line 1, in the title of the patent, "FILING" should be replaced with --FILLING--.

FIG. 11 should be replaced with the following drawing, which replaces reference numeral "128" applied to the leftmost directional arrow with reference numeral --127--.

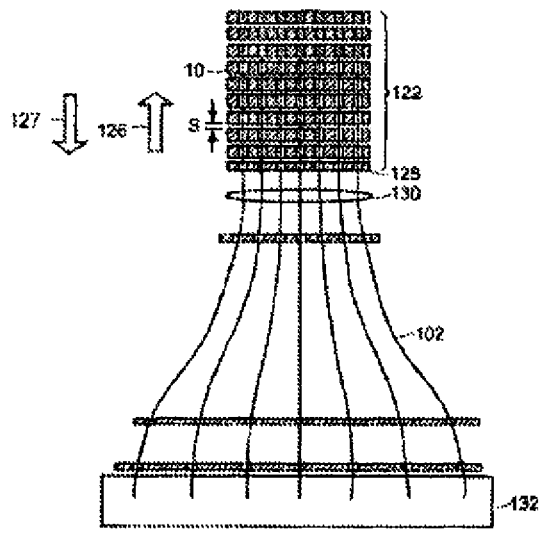

FIG. 11

In column 6, line 63, "enviroment" should be replaced with --environment--.

In column 10, line 60, "reaplication" should be replaced with --reapplication--.

In column 13, line 40, reference numeral "128" should be replaced with --127--.

This certificate supersedes the Certificate of Correction issued December 29, 2009.

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,547,556 B2 | Page 1 of 1 |
| APPLICATION NO. | : 10/958969 | |
| DATED | : June 16, 2009 | |
| INVENTOR(S) | : Hunter et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1151 days.

Signed and Sealed this
Sixteenth Day of August, 2011

David J. Kappos
*Director of the United States Patent and Trademark Office*